(12) United States Patent
Lam et al.

(10) Patent No.: US 7,994,393 B2
(45) Date of Patent: Aug. 9, 2011

(54) METHOD TO IMPROVE PLANT RESISTANCE TO INFECTIONS

(75) Inventors: Hon-Ming Lam, Hong Kong (CN); Sai Ming Samuel Sun, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 235 days.

(21) Appl. No.: 12/145,435

(22) Filed: Jun. 24, 2008

(65) Prior Publication Data

US 2010/0313296 A1  Dec. 9, 2010

Related U.S. Application Data

(60) Provisional application No. 60/947,365, filed on Jun. 29, 2007, provisional application No. 60/947,590, filed on Jul. 2, 2007.

(51) Int. Cl.
*A01H 5/00* (2006.01)
*C12N 15/09* (2006.01)
*C12N 15/82* (2006.01)

(52) U.S. Cl. ..... 800/279; 800/278; 800/298; 435/320.1; 435/468; 435/419; 435/418

(58) Field of Classification Search .................. None
See application file for complete search history.

(56) References Cited

U.S. PATENT DOCUMENTS

| 2002/0031818 A1 | 3/2002 | Ronai et al. |
| 2002/0119547 A1 | 8/2002 | Curtis et al. |
| 2006/0123505 A1* | 6/2006 | Kikuchi et al. ............... 800/278 |

OTHER PUBLICATIONS

International Search Report and Written Opinion for PCT/US08/68189, mailed Mar. 10, 2009, 7 pages.
Stone et al., Plant Physiology (2005) 137:13-30.

* cited by examiner

*Primary Examiner* — Medina A Ibrahim
(74) *Attorney, Agent, or Firm* — Morrison & Foerster LLP

(57) ABSTRACT

The disclosed invention relates to expression systems that effect production of a protein in plants that confers resistance to trauma. The expression systems are used to modify plants to improve their resistance to infections and wounding.

7 Claims, 12 Drawing Sheets

```
atgccagcccttcgcttcctcatggccgtcattgggctccttgccattcaattgttgca
 M  P  A  P  S  L  P  H  G  R  H  W  A  P  C  H  S  I  V  A
gcgccgttgcttattgcgtttgagctgctgctttgcatatatctcgaaagtttgagagtt
 A  P  L  L  I  A  F  E  L  L  L  C  I  Y  L  E  S  L  R  V
aaaagtaagccgactgttgatttgaagattgtattccttcctcttctggcctttgaagtg
 K  S  K  P  T  V  D  L  K  I  V  F  L  P  L  L  A  F  E  V
attattcttgttgacaatttcagaatgtgtagagctttaatgccaggagatgaagaaagt
 I  I  L  V  D  N  F  R  M  C  R  A  L  M  P  G  D  E  E  S
atgagcgatgaagctatttgggagacacttcctcacttttggttgcaatttctatggtg
 M  S  D  E  A  I  W  E  T  L  P  H  F  W  V  A  I  S  M  V
tttcttatagctgctacaaccttcacacttttgaagctgtctggtgatgttggtgctttg
 F  L  I  A  A  T  F  T  L  L  K  L  S  G  D  V  G  A  L
ggatggtgggatttgtttataaattatggaatcgcggagtgttttgcattcttgtttgt
 G  W  W  D  L  F  I  N  Y  G  I  A  E  C  F  A  F  L  V  C
actagatggtttaatcccatgattcataaatctcctaatcctggggaggctagctcatca
 T  R  W  F  N  P  M  I  H  K  S  P  N  P  G  E  A  S  S  S
tcagcggcaattagataccgtgattgggagagtggtcttctcctcccatcactagaagat
 S  A  A  I  R  Y  R  D  W  E  S  G  L  L  L  P  S  L  E  D
catgaacaagagaggctctgtggtcttcctgacataggcggtcacgtaatgaaaatacca
 H  E  Q  E  R  L  C  G  L  P  D  I  G  G  H  V  M  K  I  P
ctggtgattttccaagttttgctttgtatgcgcttggagggtacgcctcctagtgctcag
 L  V  I  F  Q  V  L  L  C  M  R  L  E  G  T  P  P  S  A  Q
tatattccgatatttgcactgttctccccactatttattttacaaggcgctggtgtcctt
 Y  I  P  I  F  A  L  F  S  P  L  F  I  L  Q  G  A  G  V  L
ttctctctagcaagattgttggagaaggttgttctactattacgaaatggaccagttagt
 F  S  L  A  R  L  L  E  K  V  V  L  L  R  N  G  P  V  S
cctaattaccttacaatctcatcaaaagtccgtgattgctttgcttttcttcatcgtggt
 P  N  Y  L  T  I  S  S  K  V  R  D  C  F  A  F  L  H  R  G
tcaaggcttcttggttggtggtctattgatgaaggcagcaaagaagagcaagcccggtta
 S  R  L  L  G  W  W  S  I  D  E  G  S  K  E  E  Q  A  R  L
ttctatactgaatctactgggtacaacacattttgtggctatccacctgaggtagtcagg
 F  Y  T  E  S  T  G  Y  N  T  F  C  G  Y  P  P  E  V  V  R
aaaatgcctaagagggatcttgcagaagaggtatggaggctccaagcagctttgggagag
 K  M  P  K  R  D  L  A  E  E  V  W  R  L  Q  A  A  L  G  E
caatcagaaattaccaaatgtaccaagcaggaatttgaaaggcttcaaaatgagaaggtt
 Q  S  E  I  T  K  C  T  K  Q  E  F  E  R  L  Q  N  E  K  V
ctttgtaggatttgctacgagggggagatatgcatggtcttacttccttgccggcacaga
 L  C  R  I  C  Y  E  G  E  I  C  M  V  L  L  P  C  R  H  R
acattatgcaagacttgttctgataagtgcaagaaatgtccaatctgccgtgtgcccatt
 T  L  C  K  T  C  S  D  K  C  K  K  C  P  I  C  R  V  P  I
gaagaacgcatgcccgtatatgatgtttaa
 E  E  R  M  P  V  Y  D  V  -
```

Figure 1

```
                   10        20        30        40        50        60        70        80        90
                   ....|....|....|....|....|....|....|....|....|....|....|....|....|....|....|....|....|....|
OsRHC1             ------------------------------------------------------------MPAPSLPHGRHWAPCHSIVAAPLLI
NP_564052          -------MSCRRVLKSIQALAAHSLLFCFTLLLVLKLDHTVSSSWWMVFFPLWAFHAVVARGRFSLPAPVAPRNRHWAPCHAVVATPLLV
NP_177535          -------MNCWRVLKSVQASVAHCFLFSFTLALVLKLDHSITYSWWVVCLPLWAFHAVVARGRFSLPAPIAPRNRHWAPCHAIVSTPLLI
AAW81737           -------MSCRRVLKSIQALAAHSLLFSFTLFVFKLDHTLSCSWWMVFFPLWAFHAVVARGRFSLPAPIAPRNRHWAPCHAVVATPLLV
BAE71207           -------MSWSRVLKSAQAFAAHTFLLCFTLLLLLKLDHQISSSWWIIFSPLWMFHGVVARGRFSLPAPSAPRNRHWAPCHAVVAMPLLI
NP_564945          MLVQRRVMSWRRVWKSFQAASAHCLLFSFTLLLALKLDHVVSHSWWFVFAPLWLFHAVIARGRFSLPAPSMPHDRHWAPFHSVMATPLLV
ABE90658           MLVRRRVMSWRRVFKSLQAMLAHAFLFSFSLLLVLKLDRFFLFSWWTVFFPLWLFHVVIARGRFSLPAPSMPHGRQWAPCHSVIATPLLV
AAF25982           -----------------------------------MVFFPLWAFHAVVARGRFSLPAPVAPRNRHWAPCHAVVATPLLV
Clustal Consensus                                                      :***  *:.:***  *::::  ***:

100       110       120       130       140       150       160       170       180
                   ....|....|....|....|....|....|....|....|....|....|....|....|....|....|....|....|....|....|
OsRHC1             AFELLLCIYLESLRVKSKPTVDLKIVFLPLLAFEVIILVDNFRMCRALMPGDEESMSDEAIWETLP-----------------------
NP_564052          AFELLLCIYLESSYARWPPAVSLKIAFLPLLAFELTILVDNLRMCRALMPGDDDSITDDAIWEALP-----------------------
NP_177535          AFELLLCVYLETAYADSPPAVSLKIVFLPLLAFEVIILVDNARMCRALMPGDDDSINDEAIWEALP-----------------------
AAW81737           SFELLLCIYLESSYASWPPAVSLRIASLPLLAFEVTILDNLRMCRALMPGDDDSINDEAIWEALP-----------------------
BAE71207           AFELLLCIYLESLYVRGFPAVDLKIVFLPLLTFEVIILIDNFRMCRALMPGDEERMSDEAIWETLP-----------------------
NP_564945          AFEILLCVHLEDKYV-----VDLKIVFLPLLAFEVAILIDNVRMCRTLMPGDEETMSDEAIWETLP-----------------------
ABE90658           AFELLLCIHLGSSYV-----VNLKIVFIPLIAFELAILIDNIRMCRALMPGDEENMTDEAVWETLP-----------------------
AAF25982           AFELLLCIYLESSYARWPPAVSLKIAFLPLLAFELTILVDNLRMCRALMPGDDDSITDDAIWEALPVSPLLLHKIFEGLSLRLGKINLLN
Clustal Consensus  :**:***::*     .     *.*:*. :**::**:  **:** ***.:*****::  :.*:*;**:**

190       200       210       220       230       240       250       260       270
                   ....|....|....|....|....|....|....|....|....|....|....|....|....|....|....|....|....|....|
OsRHC1             ------------------------HFWVAISMVFLIAATTFTLLKLSGDVGALGWWDLFIN----------------------
NP_564052          ------------------------HFWVAISMVFTLAATFFTLLKLSGDVVALGWWDLFIN----------------------
NP_177535          ------------------------HFWVAISMVFFLAATVFTLLKLSGDVAALGWWDLFIN----------------------
AAW81737           ------------------------HFWVAISMVFTLAATFFALLKLTGDVAALSWWDLFIN----------------------
BAE71207           ------------------------HFWVAISMVFVAATVFTLLKLSGSVASLGWWDLFIN----------------------
NP_564945          ------------------------HFWVSISMVFFIAATTFTLLKLCGDVAALGWWDLFINFG--------------------
ABE90658           ------------------------HFWISISMVFFVAATVFTLLKICGDVAALGWWDLFINYGYNQYLLVDCFKHFILILYFFHHKLILS
AAF25982           MNENLSLIFQLHNSGLRREKTLTNHFWVAISMVFTLAATFFTLLKLSVFEKYLPFLWLLVKNMKVIYMKC--------------------S
Clustal Consensus                         ***::*****  :*** *:***.        *  : *:::

280       290       300       310       320       330       340       350       360
                   ....|....|....|....|....|....|....|....|....|....|....|....|....|....|....|....|....|....|
OsRHC1             -YGIAECFAFLVCTRWFNPMIHKSPNPGEASSSSAAIRYRDWESG-LLLPSLEDHEQERLCGLPDIGGHVMKIPLVIFQVLLCMRLEGTP
NP_564052          -FGIAECFAFLVCTKWSNPVIHRSSRARETGSSSTSIRYLDWNSG-LVVAPEEDRHQDRWCGLQDIGGHMLKIPVILFQVVLCMHLEGTP
NP_177535          -FGIAECFAFLVCTKWSNPVIHRSSRDRETGSSSTNIRYLDWNSG-LGVFSEDDRNQD-TCGLQDIGGHIMKIPFVTFQIILFMRLEGTP
AAW81737           -VGIAECFAFLVCTKWSNPVIHRSSRPRETGSSSTPVRYLDWNSG-LVVTPEQDNHQDRYCGLQDIGGHLLKIPIVFQVVLCMHLEGTP
BAE71207           -FTIAECFAFLVCTKWSNPVIHRSSRE-PSSSSSTTIRYLDWNNG-LLVSSEEDQRQARICTLQDIGGHFMKVPIIVFQVLLCMHLEGTP
NP_564945          ---IAECFAFLVCTKWSNQSIHRYSHIPEPSSSKVRYLDWNRGLVVTADDEHQQSNRICGLQDIGGHVMKIPFVTFQIIFMRLEGTP
ABE90658           FCSIAQCFAFLVCTKWHNPTIHGNGHITEPCSSSNTVRYLEWSREGIVISTEEDEQQNVFCSLQDIGGHIMKIPFIAFQILLFMHLEGTP
AAF25982           ACRIAECFAFLVCTKWSNPVIHRSSRARETGSSSTSIRYLDWNSG-LVVAPEEDRHQDRWCGLQDIGGHMLKIPVILFQVVLCMYLEGTP
Clustal Consensus    **:********:* **       .    ***  :** :*.           :      * * *****.:*:*.:  **:* * *****

370       380       390       400       410       420       430       440       450
                   ....|....|....|....|....|....|....|....|....|....|....|....|....|....|....|....|....|....|
OsRHC1             PSAQYIPIFALFSPLFILQGAGVLFSLARLLEKVVLLLRNGPVSP-NYLTISSKVRDCFAFLHRGSRLLGWWSIDEGSKEEQARLFYTES
NP_564052          ERAKDISIPVLFSPLFLLQGLGVLFAASKLIVLLLRGEAGPG-LYFRFSSSAHDCLGFLHHGSRLLGWWSIDEGSREEQARLYFDQE
NP_177535          EAAKSISVPVLFSPLFLLQGVGVLFAASKLIEKVVLLLRGEDDTG-LYFRFLSRAHDCLGFLHHGSRLLGWWSIDEGSREEEARLYFDQE
AAW81737           ERAKDISIPVLFSPIFLLQGLGVLFATSKLIEKIVDLLQGEAGTG-LYFRVSSRAHDCLGFLHHGSRLLGWWSIDEGSREEQARLYFDQE
BAE71207           AFAAQLPLAVLFSPLFVLQGVGVILSASKFVEKLVLLLRSGAGGG-LYFRVSSIAHDCLGFLHHGSRLLGWWSIDEGSREEQARLYHEGA
NP_564945          ASAKNIPILVLFVPLFLLQGAGVLFAMYRLVEKSVLLINSGSGSYGRYFTATSSAREFLGFFQHGARLLGWWSIDEGSREEQARLYSGEA
ABE90658           SGAKDIPIWVIFSPLLLLQGAGVLFAAYRLIEKIILLLYNGDIPR-SYSSISSKSRDCFGFFNHGSRLLGWWSIDEGSREEEARLFCAGS
AAF25982           ERAKDISIPVLFSPLFLLQGLGVLFAASKLIEKIVLLLRGEAGPG-LYFRFSSSAHDCLGFLHHGSRLLGWWSIDEGSREEQARLYFDQE
Clustal Consensus    *  ::  :* *::*** **:::    :::** *: .        *     *  :. :.::*:************ **:***:

460       470       480       490       500       510       520       530       540
                   ....|....|....|....|....|....|....|....|....|....|....|....|....|....|....|....|....|....|
OsRHC1             TGYNTFCGYPPEVVRKMPKRDLAEEVWRLQAALGEQSEITKCTKQEFERLLQ---------------------------------NEKVLC
NP_564052          SGYNTFSGHPPEIVKKMPKEDLAEEVWRLQAALGEQTEITKFSQQEYERLQ---------------------------------NEKVLC
NP_177535          SGYNTFCGHPPEIVKKMPKKELAEEVWRLQAALGEQTEITKFSQQEYERLQ---------------------------------NEKVLC
AAW81737           SGYNTFSGHPPEIVKKMPKEDLAEEVWRLQAALGEQTEITKFSQQEYERLQ---------------------------------NEKVLC
BAE71207           SGYNTFSGYPPEIVKKMPKRDLAEEVWRLQAALGEQTEITKYSQQEYERLK---------------------------------NEKVLC
NP_564945          TGYNTFS---PEVVKKMPKSDLVEEIWRLQAALSEQTDITSYSQQEYERLQ---------------------------------NEKIIC
ABE90658           SGYNTFS---PDTVKKMPRGELVEEIWRLQAALGEQTEVTKYSQEEYERLQ---------------------------------NEKIIC
AAF25982           SGL------------VWRLQAALGEQTEITKFSQQEYERLQNVYSFISHDVFVTFLRFYFFPLLNPVSMCLLLQEKVLC
Clustal Consensus  :*         :*******.**::::*. ::::*:***:                                         :**:**

550       560       570       580
                   ....|....|....|....|....|....|....|....|
OsRHC1             RICYEGEICMVLLPCRERTLCKTCSDKCKKCPICRVPIEERMPVYDV
NP_564052          RVCFEKDISLVLLPCRERVLCRTCADKCTTCPICRIDIEKRLSVYDV
NP_177535          RVCFEREISVVLLPCRERVLCRNCSDKCKKCPFCRITIEERLPVYDV
AAW81737           RVCFEKEISLVLLPCRERVLCRICSDKCTKCPICRVAIEERLLVYDV
BAE71207           RICFEGEISVVLLPCRERVLCSLCSEKCKMCPICRNYIAERLPVYDV
NP_564945          RVCFEDPINVVLLPCRERVLCSTCEEKCKKCPICRVLIEERMPVYDV
ABE90658           RVCFEEQINVVLLPCKERVLCSTCEEKCKKCPICRGTIEERMPIYDV
AAF25982           RVCFEKDISLVLLPCRERVLCRTCADKCTTCPICRIDIEKRLSVYDV
Clustal Consensus  *:*:*  * :*****:*:.** .:**:** * :*: ***
```

Figure 2A

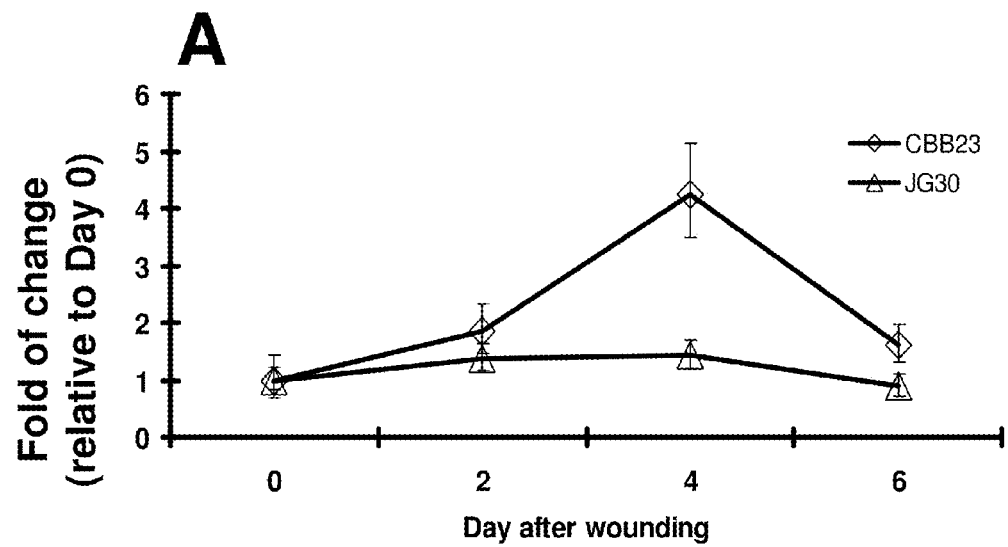
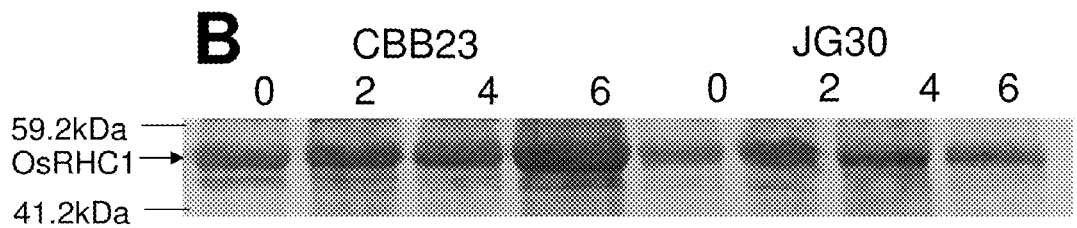
Figure 4
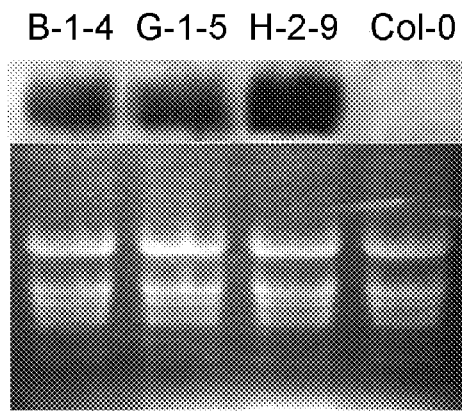
Figure 5A

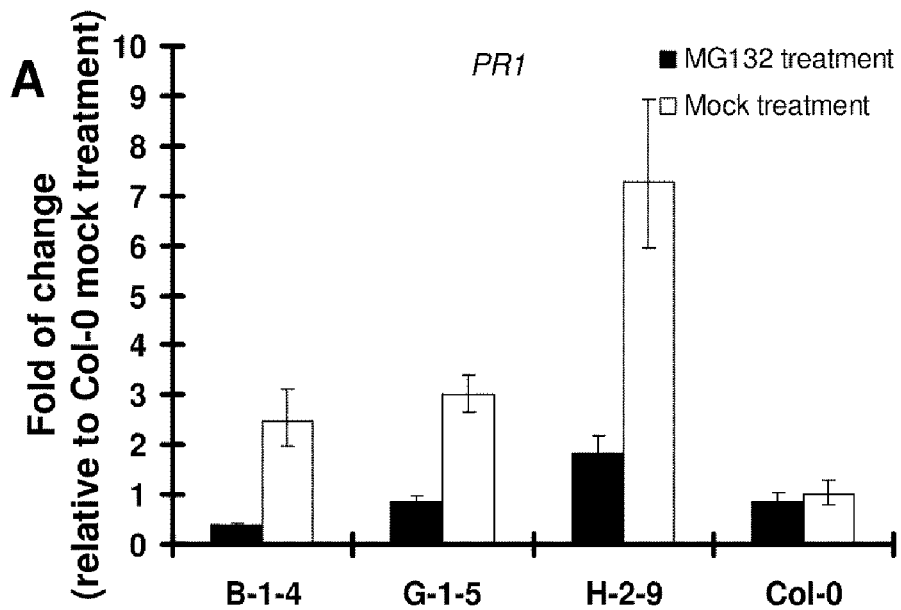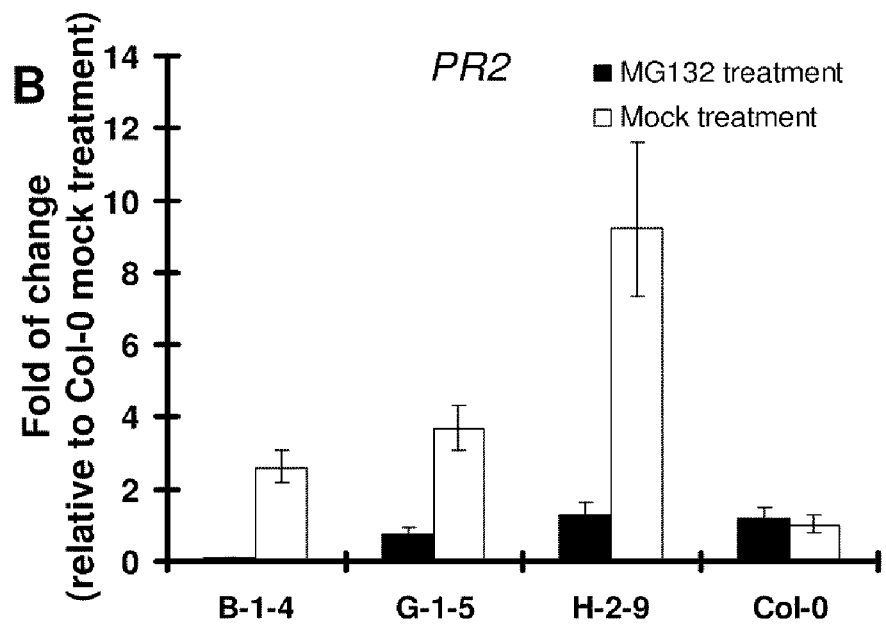
Figures 7A and B

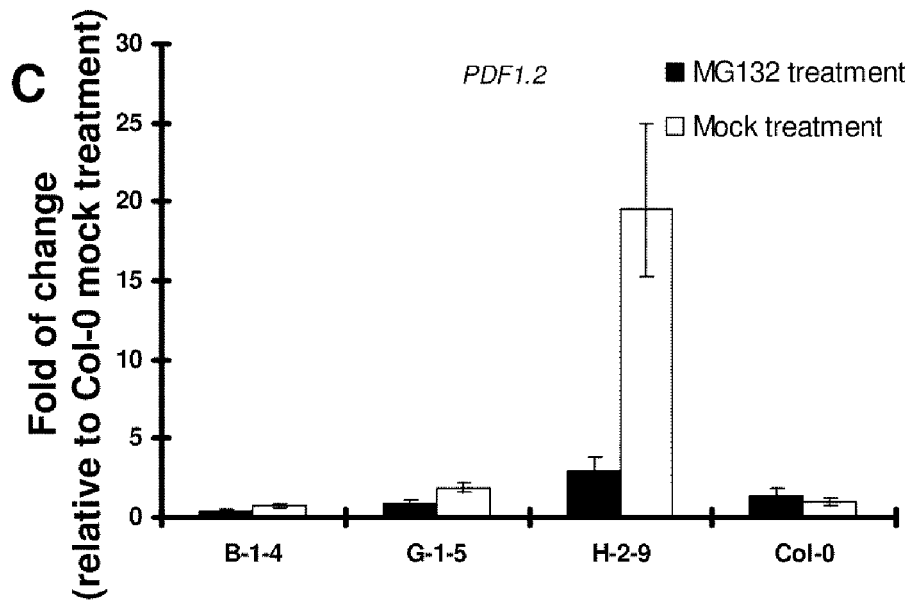
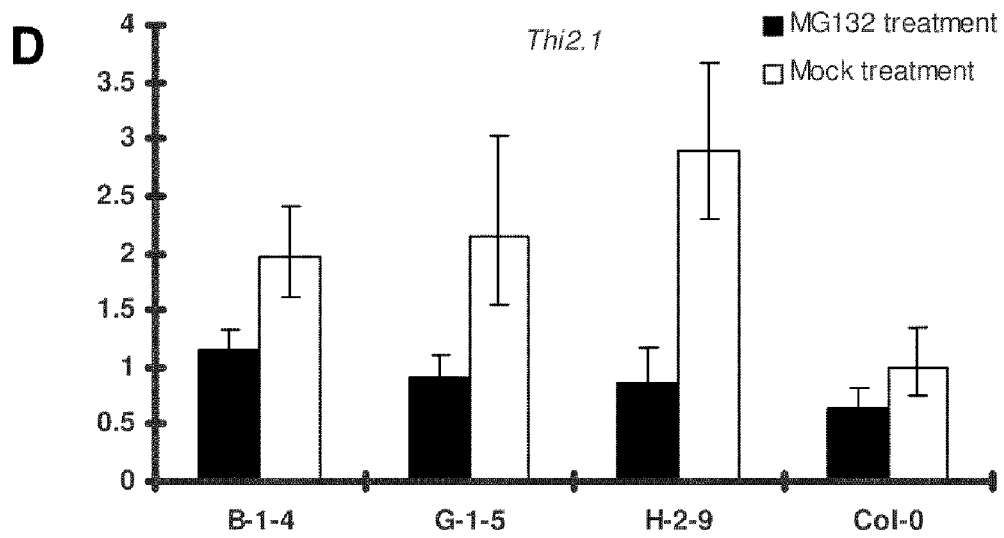
Figures 7C and D

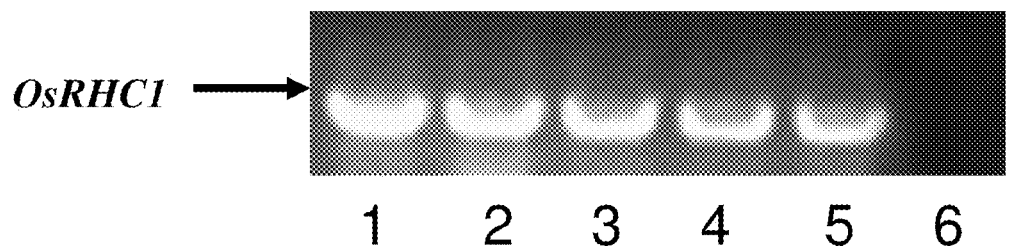
Figure 9
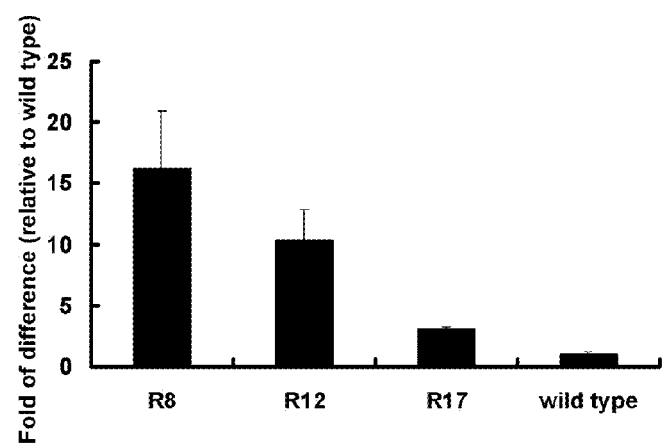
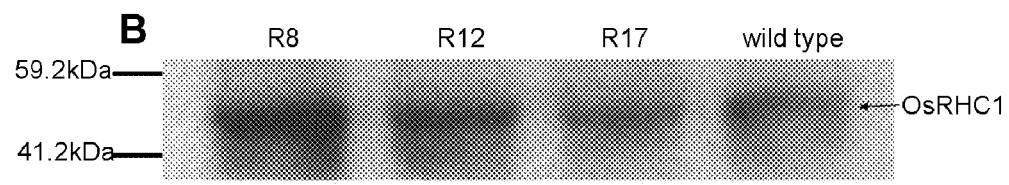
Figure 10

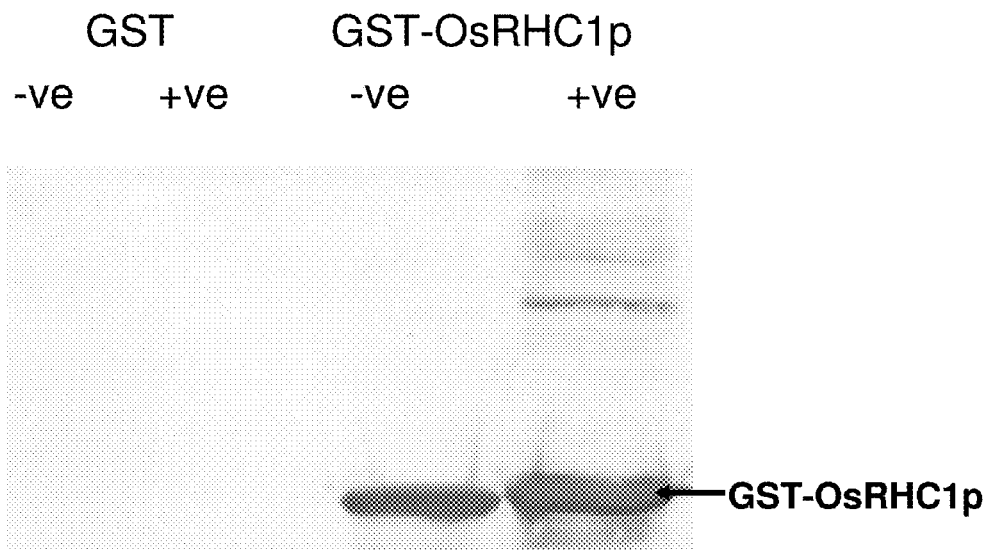

Figure 12 atggccgtggggtcagagcggctcggcgaggaggccgcccggcggcagctcggcgaggca
 M  A  V  G  S  E  R  L  G  E  E  A  A  R  R  Q  L  G  E  A
aggaaggccagaggcggctgctcggcgacgagggacggcgccgatgatgagggccggcgg
 R  K  A  R  G  G  C  S  A  T  R  D  G  A  D  D  E  G  R  R
cagataaaccctccctccccggtgtggtcgtcccctccctcactccctcttcctctcaga
 Q  I  N  P  P  S  P  V  W  S  S  P  P  S  L  P  L  P  L  R
tctgcccggaggggacgggtggaggccggcggcctcccttccctctttcctctcagatc
 S  A  R  R  G  T  G  G  R  R  P  P  F  P  L  S  S  Q  I
cgcccggtggggagaggccaccggcggcagcggcatggccctcccctctgcagcagtaga
 R  P  V  G  R  G  H  R  R  Q  R  H  G  P  P  L  C  S  S  R
gggcggcagggaggaggccacagagctgtgttttttatttgttttatttga
 G  R  Q  G  G  G  H  R  A  V  F  F  Y  L  F  L  F  -

Figure 13

SEQUENCE LISTING

```
<160> NUMBER OF SEQ ID NOS: 52

<210> SEQ ID NO 1
<211> LENGTH: 107
<212> TYPE: PRT
<213> ORGANISM: Artificial Sequence
<220> FEATURE:
<223> OTHER INFORMATION: Synthetic construct
<220> FEATURE:
<221> NAME/KEY: Misc_feature
<222> LOCATION: (1)...(107)
<223> OTHER INFORMATION: RING zing finger HC subclass consensus
<220> FEATURE:
<221> NAME/KEY: Misc_feature
<222> LOCATION: (2)...(3)
<223> OTHER INFORMATION: Xaa can be any naturally occurring amino acid
<220> FEATURE:
<221> NAME/KEY: Misc_feature
<222> LOCATION: (5)...(43)
```

```
<223> OTHER INFORMATION: Xaa can be any naturally occurring amino acid,
      up to 30 may be absent
<220> FEATURE:
<221> NAME/KEY: Misc_feature
<222> LOCATION: (45)...(47)
<223> OTHER INFORMATION: Xaa can be any naturally occurring amino acid,
      up to 2 may be absent
<220> FEATURE:
<221> NAME/KEY: Misc_feature
<222> LOCATION: (49)...(51)
<223> OTHER INFORMATION: Xaa can be any naturally occurring amino acid,
      1 may be absent
<220> FEATURE:
<221> NAME/KEY: Misc_feature
<222> LOCATION: (53)...(54)
<223> OTHER INFORMATION: Xaa can be any naturally occurring amino acid
<220> FEATURE:
<221> NAME/KEY: Misc_feature
<222> LOCATION: (56)...(103)
<223> OTHER INFORMATION: Xaa can be any naturally occurring amino acid,
      up to 44 may be absent
<220> FEATURE:
<221> NAME/KEY: Misc_feature
<222> LOCATION: (105)...(106)
<223> OTHER INFORMATION: Xaa can be any naturally occurring amino acid

<400> SEQUENCE: 1

Cys Xaa Xaa Cys Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Cys Xaa Xaa Xaa His
        35                  40                  45

Xaa Xaa Xaa Cys Xaa Xaa Cys Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Cys Xaa Xaa Cys
            100                 105

<210> SEQ ID NO 2
<211> LENGTH: 107
<212> TYPE: PRT
<213> ORGANISM: Artificial Sequence
<220> FEATURE:
<223> OTHER INFORMATION: Synthetic construct
<220> FEATURE:
<221> NAME/KEY: Misc_feature
<222> LOCATION: (1)...(107)
<223> OTHER INFORMATION: RING zing finger H2 subclass consensus
<220> FEATURE:
<221> NAME/KEY: Misc_feature
<222> LOCATION: (2)...(3)
<223> OTHER INFORMATION: Xaa can be any naturally occurring amino acid
<220> FEATURE:
<221> NAME/KEY: Misc_feature
<222> LOCATION: (5)...(43)
<223> OTHER INFORMATION: Xaa can be any naturally occurring amino acid,
      up to 30 may be absent
<220> FEATURE:
<221> NAME/KEY: Misc_feature
<222> LOCATION: (45)...(47)
<223> OTHER INFORMATION: Xaa can be any naturally occurring amino acid,
      up to 2 may be absent
<220> FEATURE:
<221> NAME/KEY: Misc_feature
<222> LOCATION: (49)...(51)
<223> OTHER INFORMATION: Xaa can be any naturally occurring amino acid,
      1 may be absent
<220> FEATURE:
```

-continued

```
<221> NAME/KEY: Misc_feature
<222> LOCATION: (53)...(54)
<223> OTHER INFORMATION: Xaa can be any naturally occurring amino acid
<220> FEATURE:
<221> NAME/KEY: Misc_feature
<222> LOCATION: (56)...(103)
<223> OTHER INFORMATION: Xaa can be any naturally occurring amino acid,
      up to 44 may be absent
<220> FEATURE:
<221> NAME/KEY: Misc_feature
<222> LOCATION: (105)...(106)
<223> OTHER INFORMATION: Xaa can be any naturally occurring amino acid

<400> SEQUENCE: 2

Cys Xaa Xaa Cys Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Cys Xaa Xaa Xaa His
        35                  40                  45

Xaa Xaa Xaa His Xaa Xaa Cys Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Cys Xaa Xaa Cys
            100                 105

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
ttctccatgt tcggtaaacc tttc                                      24

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
taaagttgtg attgagacta catgg                                     25

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
acattgcaca accaacatgt ac                                        22

<210> SEQ ID NO 6
<211> LENGTH: 19
<212> TYPE: DNA
<213> ORGANISM: Artificial Sequence
<220> FEATURE:
<223> OTHER INFORMATION: Primer
```

-continued

```
<400> SEQUENCE: 6
cctcactttt gtctcccac                                                  19

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
cgacattgca caaccaac                                                   18

<210> SEQ ID NO 8
<211> LENGTH: 35
<212> TYPE: PRT
<213> ORGANISM: Artificial Sequence
<220> FEATURE:
<223> OTHER INFORMATION: synthetic construct
<220> FEATURE:
<221> NAME/KEY: Misc_feature
<222> LOCATION: (1)...(35)
<223> OTHER INFORMATION: RING-HC domain consensus
<220> FEATURE:
<221> NAME/KEY: Misc_feature
<222> LOCATION: (1)...(35)
<223> OTHER INFORMATION: Xaa can be any naturally occurring amino acid

<400> SEQUENCE: 8

Cys Xaa Xaa Cys Xaa Xaa Xaa Xaa Xaa Xaa Xaa Xaa Xaa Xaa Xaa Cys
1               5                   10                  15

Xaa His Xaa Xaa Xaa Cys Xaa Xaa Cys Xaa Xaa Xaa Xaa Xaa Xaa Cys
            20                  25                  30

Xaa Xaa Cys
        35

<210> SEQ ID NO 9
<211> LENGTH: 17
<212> TYPE: PRT
<213> ORGANISM: Artificial Sequence
<220> FEATURE:
<223> OTHER INFORMATION: Synthetic construct

<400> SEQUENCE: 9

Asn Cys Gly Tyr Pro Pro Glu Val Val Arg Lys Met Pro Lys Arg Asp
1               5                   10                  15

Cys

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
aaagaagagc aagcccggtt at                                              22

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
```

-continued gcctccatac ctcttctgca a                                      21

<210> SEQ ID NO 12
<211> LENGTH: 26
<212> TYPE: DNA
<213> ORGANISM: Artificial Sequence
<220> FEATURE:
<223> OTHER INFORMATION: Primer

<400> SEQUENCE: 12
cttcatagga atggaagctg cgggta                                 26

<210> SEQ ID NO 13
<211> LENGTH: 25
<212> TYPE: DNA
<213> ORGANISM: Artificial Sequence
<220> FEATURE:
<223> OTHER INFORMATION: Primer

<400> SEQUENCE: 13
gaccaccttg atcttcatgc tgcta                                  25

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
tcaagatagc ccacaagatt atc                                    23

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
cttctcgttc acataattcc cac                                    23

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
accaccactg atacgtctcc tc                                     22

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
aacttcatac ttagactgtc gatc                                   24

<210> SEQ ID NO 18
<211> LENGTH: 22
<212> TYPE: DNA
<213> ORGANISM: Artificial Sequence
<220> FEATURE:

<223> OTHER INFORMATION: Primer

<400> SEQUENCE: 18
cccttatctt cgctgctctt gt                                              22

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
ccctgaccat gtcccacttg                                                 20

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
agcactgcaa gttagggtgt ga                                              22

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
acattgttcc gacgctccat                                                 20

<210> SEQ ID NO 22
<211> LENGTH: 19
<212> TYPE: DNA
<213> ORGANISM: Artificial Sequence
<220> FEATURE:
<223> OTHER INFORMATION: Primer

<400> SEQUENCE: 22
gaaggtgctg agttgattg                                                  19

<210> SEQ ID NO 23
<211> LENGTH: 18
<212> TYPE: DNA
<213> ORGANISM: Artificial Sequence
<220> FEATURE:
<223> OTHER INFORMATION: Primer

<400> SEQUENCE: 23
ggacttgacg ttgtttgg                                                   18

<210> SEQ ID NO 24
<211> LENGTH: 20
<212> TYPE: DNA
<213> ORGANISM: Artificial Sequence
<220> FEATURE:
<223> OTHER INFORMATION: Forward primer

<400> SEQUENCE: 24
ctgatgcata tacatgatgg                                                 20

<210> SEQ ID NO 25

```
<211> LENGTH: 22
<212> TYPE: DNA
<213> ORGANISM: Artificial Sequence
<220> FEATURE:
<223> OTHER INFORMATION: Reverse primer

<400> SEQUENCE: 25
acattgcaca accaacatgt ac                                              22

<210> SEQ ID NO 26
<211> LENGTH: 22
<212> TYPE: DNA
<213> ORGANISM: Artificial Sequence
<220> FEATURE:
<223> OTHER INFORMATION: Forward primer

<400> SEQUENCE: 26
aaagaagagc aagcccggtt at                                              22

<210> SEQ ID NO 27
<211> LENGTH: 21
<212> TYPE: DNA
<213> ORGANISM: Artificial Sequence
<220> FEATURE:
<223> OTHER INFORMATION: Reverse primer

<400> SEQUENCE: 27
gcctccatac ctcttctgca a                                               21

<210> SEQ ID NO 28
<211> LENGTH: 26
<212> TYPE: DNA
<213> ORGANISM: Artificial Sequence
<220> FEATURE:
<223> OTHER INFORMATION: Forward primer

<400> SEQUENCE: 28
cggacagagg ccttactaag ttattt                                          26

<210> SEQ ID NO 29
<211> LENGTH: 28
<212> TYPE: DNA
<213> ORGANISM: Artificial Sequence
<220> FEATURE:
<223> OTHER INFORMATION: Reverse primer

<400> SEQUENCE: 29
gacctgttta cattttcacg tctttatt                                        28

<210> SEQ ID NO 30
<211> LENGTH: 21
<212> TYPE: DNA
<213> ORGANISM: Artificial Sequence
<220> FEATURE:
<223> OTHER INFORMATION: Forward primer

<400> SEQUENCE: 30
gaggcaacgg acaccactaa g                                               21

<210> SEQ ID NO 31
<211> LENGTH: 25
<212> TYPE: DNA
<213> ORGANISM: Artificial Sequence
<220> FEATURE:
<223> OTHER INFORMATION: Reverse primer

<400> SEQUENCE: 31
```
tgtaaagcag agagagaggc tcatt                                         25

<210> SEQ ID NO 32
<211> LENGTH: 20
<212> TYPE: DNA
<213> ORGANISM: Artificial Sequence
<220> FEATURE:
<223> OTHER INFORMATION: Forward primer

<400> SEQUENCE: 32
aagctcaagt cacactcgac                                               20

<210> SEQ ID NO 33
<211> LENGTH: 19
<212> TYPE: DNA
<213> ORGANISM: Artificial Sequence
<220> FEATURE:
<223> OTHER INFORMATION: Reverse primer

<400> SEQUENCE: 33
gatgtccttc tccttctcc                                                19

<210> SEQ ID NO 34
<211> LENGTH: 26
<212> TYPE: DNA
<213> ORGANISM: Artificial Sequence
<220> FEATURE:
<223> OTHER INFORMATION: Forward primer

<400> SEQUENCE: 34
cttcatagga atggaagctg cgggta                                        26

<210> SEQ ID NO 35
<211> LENGTH: 25
<212> TYPE: DNA
<213> ORGANISM: Artificial Sequence
<220> FEATURE:
<223> OTHER INFORMATION: Reverse primer

<400> SEQUENCE: 35
gaccaccttg atcttcatgc tgcta                                         25

<210> SEQ ID NO 36
<211> LENGTH: 32
<212> TYPE: DNA
<213> ORGANISM: Artificial Sequence
<220> FEATURE:
<223> OTHER INFORMATION: Primer

<400> SEQUENCE: 36
ccggaattcg ttgttctact attacgaaat gg                                 32

<210> SEQ ID NO 37
<211> LENGTH: 32
<212> TYPE: DNA
<213> ORGANISM: Artificial Sequence
<220> FEATURE:
<223> OTHER INFORMATION: Primer

<400> SEQUENCE: 37
caggtcgacg ttaaacatca tatacgggca tg                                 32

<210> SEQ ID NO 38
<211> LENGTH: 27
<212> TYPE: DNA
<213> ORGANISM: Artificial Sequence
<220> FEATURE:

-continued

<223> OTHER INFORMATION: Primer

<400> SEQUENCE: 38
ccgaattcat gccagcccct tcgcttc                                          27

<210> SEQ ID NO 39
<211> LENGTH: 32
<212> TYPE: DNA
<213> ORGANISM: Artificial Sequence
<220> FEATURE:
<223> OTHER INFORMATION: Primer

<400> SEQUENCE: 39
caggtcgacg ttaaacatca tatacgggca tg                                    32

<210> SEQ ID NO 40
<211> LENGTH: 26
<212> TYPE: DNA
<213> ORGANISM: Artificial Sequence
<220> FEATURE:
<223> OTHER INFORMATION: Primer

<400> SEQUENCE: 40
aacccgggat ggccgtgggg tcagag                                           26

<210> SEQ ID NO 41
<211> LENGTH: 35
<212> TYPE: DNA
<213> ORGANISM: Artificial Sequence
<220> FEATURE:
<223> OTHER INFORMATION: Primer

<400> SEQUENCE: 41
ttcccgggtc aaaataaaaa caaataaaaa aacac                                 35

<210> SEQ ID NO 42
<211> LENGTH: 1230
<212> TYPE: DNA
<213> ORGANISM: Artificial Sequence
<220> FEATURE:
<223> OTHER INFORMATION: Synthetic construct
<220> FEATURE:
<221> NAME/KEY: Misc_feature
<222> LOCATION: (1)...(1230)
<223> OTHER INFORMATION: RING zinc finger protein gene (OsRHC1)
<220> FEATURE:
<221> NAME/KEY: CDS
<222> LOCATION: (1)...(1230)

<400> SEQUENCE: 42

```
atg cca gcc cct tcg ctt cct cat ggc cgt cat tgg gct cct tgc cat       48
Met Pro Ala Pro Ser Leu Pro His Gly Arg His Trp Ala Pro Cys His
1               5                   10                  15 tca att gtt gca gcg ccg ttg ctt att gcg ttt gag ctg ctg ctt tgc       96
Ser Ile Val Ala Ala Pro Leu Leu Ile Ala Phe Glu Leu Leu Leu Cys
            20                  25                  30 ata tat ctc gaa agt ttg aga gtt aaa agt aag ccg act gtt gat ttg      144
Ile Tyr Leu Glu Ser Leu Arg Val Lys Ser Lys Pro Thr Val Asp Leu
        35                  40                  45 aag att gta ttc ctt cct ctt ctg gcc ttt gaa gtg att att ctt gtt      192
Lys Ile Val Phe Leu Pro Leu Leu Ala Phe Glu Val Ile Ile Leu Val
    50                  55                  60 gac aat ttc aga atg tgt aga gct tta atg cca gga gat gaa gaa agt      240
Asp Asn Phe Arg Met Cys Arg Ala Leu Met Pro Gly Asp Glu Glu Ser
65                  70                  75                  80 atg agc gat gaa gct att tgg gag aca ctt cct cac ttt tgg gtt gca      288
```

-continued

| | | |
|---|---|---|
| Met Ser Asp Glu Ala Ile Trp Glu Thr Leu Pro His Phe Trp Val Ala<br>85 90 95 | | |
| att tct atg gtg ttt ctt ata gct gct aca acc ttc aca ctt ttg aag<br>Ile Ser Met Val Phe Leu Ile Ala Ala Thr Thr Phe Thr Leu Leu Lys<br>100 105 110 | 336 | |
| ctg tct ggt gat gtt ggt gct ttg gga tgg tgg gat ttg ttt ata aat<br>Leu Ser Gly Asp Val Gly Ala Leu Gly Trp Trp Asp Leu Phe Ile Asn<br>115 120 125 | 384 | |
| tat gga atc gcg gag tgt ttt gca ttt ctt gtt tgt act aga tgg ttt<br>Tyr Gly Ile Ala Glu Cys Phe Ala Phe Leu Val Cys Thr Arg Trp Phe<br>130 135 140 | 432 | |
| aat ccc atg att cat aaa tct cct aat cct ggg gag gct agc tca tca<br>Asn Pro Met Ile His Lys Ser Pro Asn Pro Gly Glu Ala Ser Ser Ser<br>145 150 155 160 | 480 | |
| tca gcg gca att aga tac cgt gat tgg gag agt ggt ctt ctc ctc cca<br>Ser Ala Ala Ile Arg Tyr Arg Asp Trp Glu Ser Gly Leu Leu Leu Pro<br>165 170 175 | 528 | |
| tca cta gaa gat cat gaa caa gag agg ctc tgt ggt ctt cct gac ata<br>Ser Leu Glu Asp His Glu Gln Glu Arg Leu Cys Gly Leu Pro Asp Ile<br>180 185 190 | 576 | |
| ggc ggt cac gta atg aaa ata cca ctg gtg att ttc caa gtt ttg ctt<br>Gly Gly His Val Met Lys Ile Pro Leu Val Ile Phe Gln Val Leu Leu<br>195 200 205 | 624 | |
| tgt atg cgc ttg gag ggt acg cct cct agt gct cag tat att ccg ata<br>Cys Met Arg Leu Glu Gly Thr Pro Pro Ser Ala Gln Tyr Ile Pro Ile<br>210 215 220 | 672 | |
| ttt gca ctg ttc tcc cca cta ttt att tta caa ggc gct ggt gtc ctt<br>Phe Ala Leu Phe Ser Pro Leu Phe Ile Leu Gln Gly Ala Gly Val Leu<br>225 230 235 240 | 720 | |
| ttc tct cta gca aga ttg ttg gag aag gtt gtt cta cta tta cga aat<br>Phe Ser Leu Ala Arg Leu Leu Glu Lys Val Val Leu Leu Leu Arg Asn<br>245 250 255 | 768 | |
| gga cca gtt agt cct aat tac ctt aca atc tca tca aaa gtc cgt gat<br>Gly Pro Val Ser Pro Asn Tyr Leu Thr Ile Ser Ser Lys Val Arg Asp<br>260 265 270 | 816 | |
| tgc ttt gct ttt ctt cat cgt ggt tca agg ctt ctt ggt tgg tgg tct<br>Cys Phe Ala Phe Leu His Arg Gly Ser Arg Leu Leu Gly Trp Trp Ser<br>275 280 285 | 864 | |
| att gat gaa ggc agc aaa gaa gag caa gcc cgg tta ttc tat act gaa<br>Ile Asp Glu Gly Ser Lys Glu Glu Gln Ala Arg Leu Phe Tyr Thr Glu<br>290 295 300 | 912 | |
| tct act ggg tac aac aca ttt tgt ggc tat cca cct gag gta gtc agg<br>Ser Thr Gly Tyr Asn Thr Phe Cys Gly Tyr Pro Pro Glu Val Val Arg<br>305 310 315 320 | 960 | |
| aaa atg cct aag agg gat ctt gca gaa gag gta tgg agg ctc caa gca<br>Lys Met Pro Lys Arg Asp Leu Ala Glu Glu Val Trp Arg Leu Gln Ala<br>325 330 335 | 1008 | |
| gct ttg gga gag caa tca gaa att acc aaa tgt acc aag cag gaa ttt<br>Ala Leu Gly Glu Gln Ser Glu Ile Thr Lys Cys Thr Lys Gln Glu Phe<br>340 345 350 | 1056 | |
| gaa agg ctt caa aat gag aag gtt ctt tgt agg att tgc tac gag ggg<br>Glu Arg Leu Gln Asn Glu Lys Val Leu Cys Arg Ile Cys Tyr Glu Gly<br>355 360 365 | 1104 | |
| gag ata tgc atg gtc tta ctt cct tgc cgg cac aga aca tta tgc aag<br>Glu Ile Cys Met Val Leu Leu Pro Cys Arg His Arg Thr Leu Cys Lys<br>370 375 380 | 1152 | |
| act tgt tct gat aag tgc aag aaa tgt cca atc tgc cgt gtg ccc att<br>Thr Cys Ser Asp Lys Cys Lys Lys Cys Pro Ile Cys Arg Val Pro Ile<br>385 390 395 400 | 1200 | |
| gaa gaa cgc atg ccc gta tat gat gtt taa | 1230 | |

Glu Glu Arg Met Pro Val Tyr Asp Val
                405

<210> SEQ ID NO 43
<211> LENGTH: 409
<212> TYPE: PRT
<213> ORGANISM: Artificial Sequence
<220> FEATURE:
<223> OTHER INFORMATION: Synthetic construct
<220> FEATURE:
<221> NAME/KEY: Misc_feature
<222> LOCATION: (1)...(409)
<223> OTHER INFORMATION: RING zinc finger protein gene (OsRHC1)

<400> SEQUENCE: 43

Met Pro Ala Pro Ser Leu Pro His Gly Arg His Trp Ala Pro Cys His
1               5                   10                  15

Ser Ile Val Ala Ala Pro Leu Leu Ile Ala Phe Glu Leu Leu Leu Cys
                20                  25                  30

Ile Tyr Leu Glu Ser Leu Arg Val Lys Ser Lys Pro Thr Val Asp Leu
            35                  40                  45

Lys Ile Val Phe Leu Pro Leu Leu Ala Phe Glu Val Ile Ile Leu Val
50                  55                  60

Asp Asn Phe Arg Met Cys Arg Ala Leu Met Pro Gly Asp Glu Glu Ser
65                  70                  75                  80

Met Ser Asp Glu Ala Ile Trp Glu Thr Leu Pro His Phe Trp Val Ala
                85                  90                  95

Ile Ser Met Val Phe Leu Ile Ala Ala Thr Thr Phe Thr Leu Leu Lys
            100                 105                 110

Leu Ser Gly Asp Val Gly Ala Leu Gly Trp Trp Asp Leu Phe Ile Asn
        115                 120                 125

Tyr Gly Ile Ala Glu Cys Phe Ala Phe Leu Val Cys Thr Arg Trp Phe
130                 135                 140

Asn Pro Met Ile His Lys Ser Pro Asn Pro Gly Glu Ala Ser Ser Ser
145                 150                 155                 160

Ser Ala Ala Ile Arg Tyr Arg Asp Trp Glu Ser Gly Leu Leu Leu Pro
                165                 170                 175

Ser Leu Glu Asp His Glu Gln Glu Arg Leu Cys Gly Leu Pro Asp Ile
            180                 185                 190

Gly Gly His Val Met Lys Ile Pro Leu Val Ile Phe Gln Val Leu Leu
        195                 200                 205

Cys Met Arg Leu Glu Gly Thr Pro Pro Ser Ala Gln Tyr Ile Pro Ile
210                 215                 220

Phe Ala Leu Phe Ser Pro Leu Phe Ile Leu Gln Gly Ala Gly Val Leu
225                 230                 235                 240

Phe Ser Leu Ala Arg Leu Leu Glu Lys Val Val Leu Leu Leu Arg Asn
                245                 250                 255

Gly Pro Val Ser Pro Asn Tyr Leu Thr Ile Ser Ser Lys Val Arg Asp
            260                 265                 270

Cys Phe Ala Phe Leu His Arg Gly Ser Arg Leu Leu Gly Trp Trp Ser
        275                 280                 285

Ile Asp Glu Gly Ser Lys Glu Glu Gln Ala Arg Leu Phe Tyr Thr Glu
290                 295                 300

Ser Thr Gly Tyr Asn Thr Phe Cys Gly Tyr Pro Glu Val Val Arg
305                 310                 315                 320

Lys Met Pro Lys Arg Asp Leu Ala Glu Glu Val Trp Arg Leu Gln Ala
                325                 330                 335

```
Ala Leu Gly Glu Gln Ser Glu Ile Thr Lys Cys Thr Lys Gln Glu Phe
            340                 345                 350

Glu Arg Leu Gln Asn Glu Lys Val Leu Cys Arg Ile Cys Tyr Glu Gly
            355                 360                 365

Glu Ile Cys Met Val Leu Leu Pro Cys Arg His Arg Thr Leu Cys Lys
            370                 375                 380

Thr Cys Ser Asp Lys Cys Lys Cys Pro Ile Cys Arg Val Pro Ile
385                 390                 395                 400

Glu Glu Arg Met Pro Val Tyr Asp Val
            405

<210> SEQ ID NO 44
<211> LENGTH: 467
<212> TYPE: PRT
<213> ORGANISM: Artificial Sequence
<220> FEATURE:
<223> OTHER INFORMATION: Synthetic construct
<220> FEATURE:
<221> NAME/KEY: Misc_feature
<222> LOCATION: (1)...(467)
<223> OTHER INFORMATION: Annotated protein NP-564052

<400> SEQUENCE: 44

Met Ser Cys Arg Arg Val Leu Lys Ser Ile Gln Ala Leu Ala Ala His
1               5                   10                  15

Ser Leu Leu Phe Cys Phe Thr Leu Leu Val Leu Lys Leu Asp His
            20                  25                  30

Thr Val Ser Ser Ser Trp Trp Met Val Phe Phe Pro Leu Trp Ala Phe
            35                  40                  45

His Ala Val Val Ala Arg Gly Arg Phe Ser Leu Pro Ala Pro Val Ala
        50                  55                  60

Pro Arg Asn Arg His Trp Ala Pro Cys His Ala Val Val Ala Thr Pro
65                  70                  75                  80

Leu Leu Val Ala Phe Glu Leu Leu Cys Ile Tyr Leu Glu Ser Ser
            85                  90                  95

Tyr Ala Arg Trp Pro Pro Ala Val Ser Leu Lys Ile Ala Phe Leu Pro
            100                 105                 110

Leu Leu Ala Phe Glu Leu Thr Ile Leu Val Asp Asn Leu Arg Met Cys
            115                 120                 125

Arg Ala Leu Met Pro Gly Asp Asp Ser Ile Thr Asp Ala Ile
        130                 135                 140

Trp Glu Ala Leu Pro His Phe Trp Val Ala Ile Ser Met Val Phe Thr
145                 150                 155                 160

Leu Ala Ala Thr Phe Phe Thr Leu Leu Lys Leu Ser Gly Asp Val Val
            165                 170                 175

Ala Leu Gly Trp Trp Asp Leu Phe Ile Asn Phe Gly Ile Ala Glu Cys
            180                 185                 190

Phe Ala Phe Leu Val Cys Thr Lys Trp Ser Asn Pro Val Ile His Arg
            195                 200                 205

Ser Ser Arg Ala Arg Glu Thr Gly Ser Ser Ser Thr Ser Ile Arg Tyr
        210                 215                 220

Leu Asp Trp Asn Ser Gly Leu Val Val Ala Pro Glu Glu Asp Arg His
225                 230                 235                 240

Gln Asp Arg Trp Cys Gly Leu Gln Asp Ile Gly Gly His Met Leu Lys
            245                 250                 255

Ile Pro Val Ile Leu Phe Gln Val Leu Cys Met Tyr Leu Glu Gly
            260                 265                 270
```

```
Thr Pro Glu Arg Ala Lys Asp Ile Ser Ile Pro Val Leu Phe Ser Pro
        275                 280                 285

Leu Phe Leu Leu Gln Gly Leu Gly Val Leu Phe Ala Ala Ser Lys Leu
290                 295                 300

Leu Glu Lys Ile Val Leu Leu Arg Gly Glu Ala Gly Pro Gly Leu
305                 310                 315                 320

Tyr Phe Arg Phe Ser Ser Ser Ala His Asp Cys Leu Gly Phe Leu His
                325                 330                 335

His Gly Ser Arg Leu Leu Gly Trp Trp Ser Ile Asp Glu Gly Ser Arg
                340                 345                 350

Glu Glu Gln Ala Arg Leu Tyr Phe Asp Gln Ser Gly Tyr Asn Thr
            355                 360                 365

Phe Ser Gly His Pro Pro Glu Ile Val Lys Lys Met Pro Lys Glu Asp
370                 375                 380

Leu Ala Glu Glu Val Trp Arg Leu Gln Ala Ala Leu Gly Glu Gln Thr
385                 390                 395                 400

Glu Ile Thr Lys Phe Ser Gln Gln Glu Tyr Glu Arg Leu Gln Asn Glu
                405                 410                 415

Lys Val Leu Cys Arg Val Cys Phe Glu Lys Asp Ile Ser Leu Val Leu
                420                 425                 430

Leu Pro Cys Arg His Arg Val Leu Cys Arg Thr Cys Ala Asp Lys Cys
                435                 440                 445

Thr Thr Cys Pro Ile Cys Arg Ile Asp Ile Glu Lys Arg Leu Ser Val
        450                 455                 460

Tyr Asp Val
465

<210> SEQ ID NO 45
<211> LENGTH: 466
<212> TYPE: PRT
<213> ORGANISM: Artificial Sequence
<220> FEATURE:
<223> OTHER INFORMATION: Synthetic construct
<220> FEATURE:
<221> NAME/KEY: Misc_feature
<222> LOCATION: (1)...(466)
<223> OTHER INFORMATION: Annotated protein NP-177535

<400> SEQUENCE: 45

Met Asn Cys Trp Arg Val Leu Lys Ser Val Gln Ala Ser Val Ala His
1               5                   10                  15

Cys Phe Leu Phe Ser Phe Thr Leu Ala Leu Val Leu Lys Leu Asp His
                20                  25                  30

Ser Ile Thr Tyr Ser Trp Trp Val Val Cys Leu Pro Leu Trp Ala Phe
            35                  40                  45

His Ala Val Val Ala Arg Gly Arg Phe Ser Leu Pro Ala Pro Ile Ala
        50                  55                  60

Pro Arg Asn Arg His Trp Ala Pro Cys His Ala Ile Val Ser Thr Pro
65                  70                  75                  80

Leu Leu Ile Ala Phe Glu Leu Leu Cys Val Tyr Leu Glu Thr Ala
                85                  90                  95

Tyr Ala Asp Ser Pro Pro Ala Val Ser Leu Lys Ile Val Phe Leu Pro
                100                 105                 110

Leu Leu Ala Phe Glu Val Ile Ile Leu Val Asp Asn Ala Arg Met Cys
            115                 120                 125

Arg Ala Leu Met Pro Gly Asp Glu Glu Ser Val Asn Asp Glu Ala Val
130                 135                 140
```

```
Trp Glu Ala Leu Pro His Phe Trp Val Ala Ile Ser Met Val Phe Phe
145                 150                 155                 160

Leu Ala Ala Thr Val Phe Thr Leu Leu Lys Leu Ser Gly Asp Val Ala
                165                 170                 175

Ala Leu Gly Trp Trp Asp Leu Phe Ile Asn Phe Gly Ile Ala Glu Cys
            180                 185                 190

Phe Ala Phe Leu Val Cys Thr Lys Trp Ser Asn Pro Val Ile His Arg
        195                 200                 205

Ser Ser Arg Asp Arg Glu Thr Gly Ser Ser Thr Asn Ile Arg Tyr
    210                 215                 220

Leu Asp Trp Asn Ser Gly Leu Gly Val Phe Ser Glu Asp Arg Asn
225                 230                 235                 240

Gln Asp Thr Cys Gly Leu Gln Asp Ile Gly Gly His Ile Met Lys Ile
                245                 250                 255

Pro Leu Ile Val Phe Gln Val Val Leu Cys Met His Leu Glu Gly Thr
                260                 265                 270

Pro Glu Ala Ala Lys Ser Ile Ser Val Pro Val Leu Phe Ser Pro Leu
                275                 280                 285

Phe Leu Leu Gln Gly Val Gly Val Leu Phe Ala Ala Ser Lys Leu Ile
            290                 295                 300

Glu Lys Val Val Leu Leu Arg Gly Glu Asp Asp Thr Gly Leu Tyr
305                 310                 315                 320

Phe Arg Phe Leu Ser Arg Ala His Asp Cys Leu Gly Phe Leu His His
                325                 330                 335

Gly Ser Arg Leu Leu Gly Trp Trp Ser Ile Asp Glu Gly Ser Arg Glu
            340                 345                 350

Glu Glu Ala Arg Leu Tyr Phe Asp Gln Glu Ser Gly Tyr Asn Thr Phe
            355                 360                 365

Cys Gly His Pro Pro Glu Ile Val Lys Lys Met Pro Lys Lys Glu Leu
        370                 375                 380

Ala Glu Glu Val Trp Arg Leu Gln Ala Ala Leu Gly Glu Gln Thr Glu
385                 390                 395                 400

Ile Thr Lys Phe Ser Gln Gln Glu Tyr Glu Arg Leu Gln Asn Glu Lys
                405                 410                 415

Val Leu Cys Arg Val Cys Phe Glu Arg Glu Ile Ser Val Val Leu Leu
            420                 425                 430

Pro Cys Arg His Arg Val Leu Cys Arg Asn Cys Ser Asp Lys Cys Lys
        435                 440                 445

Lys Cys Pro Phe Cys Arg Ile Thr Ile Glu Glu Arg Leu Pro Val Tyr
    450                 455                 460

Asp Val
465

<210> SEQ ID NO 46
<211> LENGTH: 467
<212> TYPE: PRT
<213> ORGANISM: Artificial Sequence
<220> FEATURE:
<223> OTHER INFORMATION: Synthetic construct
<220> FEATURE:
<221> NAME/KEY: Misc_feature
<222> LOCATION: (1)...(467)
<223> OTHER INFORMATION: Annotated protein AAW81737

<400> SEQUENCE: 46

Met Ser Cys Arg Arg Val Leu Lys Ser Ile Gln Ala Leu Ala Ala His
1               5                   10                  15
```

```
Ser Leu Leu Phe Ser Phe Thr Leu Phe Leu Val Phe Lys Leu Asp His
            20              25              30

Thr Leu Ser Cys Ser Trp Trp Met Val Phe Pro Leu Trp Ala Phe
        35              40              45

His Ala Val Val Ala Arg Gly Arg Phe Ser Leu Pro Ala Pro Ile Ala
 50              55              60

Pro Arg Asn Arg His Trp Ala Pro Cys His Ala Val Val Ala Thr Pro
 65              70              75              80

Leu Leu Val Ser Phe Glu Leu Leu Leu Cys Ile Tyr Leu Glu Ser Ser
                85              90              95

Tyr Ala Ser Trp Pro Pro Ala Val Ser Leu Arg Ile Ala Ser Leu Pro
            100             105             110

Leu Leu Ala Phe Glu Val Thr Ile Leu Ile Asp Asn Leu Arg Met Cys
        115             120             125

Arg Ala Leu Met Pro Gly Asp Asp Ser Ile Asn Asp Glu Ala Ile
130             135             140

Trp Glu Ala Leu Pro His Phe Trp Val Ala Ile Ser Met Val Phe Thr
145             150             155             160

Leu Ala Ala Thr Phe Phe Ala Leu Leu Lys Leu Thr Gly Asp Val Ala
            165             170             175

Ala Leu Ser Trp Trp Asp Leu Phe Ile Asn Val Gly Ile Ala Glu Cys
        180             185             190

Phe Ala Phe Leu Val Cys Thr Lys Trp Ser Asn Pro Val Ile His Arg
    195             200             205

Ser Ser Arg Pro Arg Glu Thr Gly Ser Ser Ser Thr Pro Val Arg Tyr
    210             215             220

Leu Asp Trp Asn Ser Gly Leu Val Val Thr Pro Glu Gln Asp Asn His
225             230             235             240

Gln Asp Arg Tyr Cys Gly Leu Gln Asp Ile Gly Gly His Leu Leu Lys
            245             250             255

Ile Pro Val Ile Val Phe Gln Val Val Leu Cys Met His Leu Glu Gly
        260             265             270

Thr Pro Glu Arg Ala Lys Asp Ile Ser Ile Pro Val Leu Phe Ser Pro
    275             280             285

Ile Phe Leu Leu Gln Gly Leu Gly Val Leu Phe Ala Thr Ser Lys Leu
290             295             300

Ile Glu Lys Ile Val Asp Leu Leu Gln Gly Glu Ala Gly Thr Gly Leu
305             310             315             320

Tyr Phe Arg Val Ser Ser Arg Ala His Asp Cys Leu Gly Phe Leu His
            325             330             335

His Gly Ser Arg Leu Leu Gly Trp Trp Ser Ile Asp Glu Gly Ser Arg
        340             345             350

Glu Glu Gln Ala Arg Leu Tyr Phe Asp Gln Glu Ser Gly Tyr Asn Thr
    355             360             365

Phe Ser Gly His Pro Pro Glu Ile Val Lys Lys Met Pro Lys Glu Asp
    370             375             380

Leu Ala Glu Glu Val Trp Arg Leu Gln Ala Ala Leu Gly Glu Gln Thr
385             390             395             400

Glu Ile Thr Lys Phe Ser Gln Gln Glu Tyr Glu Arg Leu Gln Asn Glu
            405             410             415

Lys Val Leu Cys Arg Val Cys Phe Glu Lys Glu Ile Ser Leu Val Leu
        420             425             430

Leu Pro Cys Arg His Arg Val Leu Cys Arg Ile Cys Ser Asp Lys Cys
    435             440             445
```

-continued

```
Thr Lys Cys Pro Ile Cys Arg Val Ala Ile Glu Glu Arg Leu Leu Val
    450                 455                 460

Tyr Asp Val
465

<210> SEQ ID NO 47
<211> LENGTH: 466
<212> TYPE: PRT
<213> ORGANISM: Artificial Sequence
<220> FEATURE:
<223> OTHER INFORMATION: Synthetic construct
<220> FEATURE:
<221> NAME/KEY: Misc_feature
<222> LOCATION: (1)...(466)
<223> OTHER INFORMATION: Annotated protein BAE71207

<400> SEQUENCE: 47

Met Ser Trp Ser Arg Val Leu Lys Ser Ala Gln Ala Phe Ala Ala His
1               5                   10                  15

Thr Phe Leu Leu Cys Phe Thr Leu Leu Leu Leu Lys Leu Asp His
            20                  25                  30

Gln Ile Ser Ser Ser Trp Trp Ile Phe Ser Pro Leu Trp Met Phe
        35                  40                  45

His Gly Val Val Ala Arg Gly Arg Phe Ser Leu Pro Ala Pro Ser Ala
    50                  55                  60

Pro Arg Asn Arg His Trp Ala Pro Cys His Ala Val Val Ala Met Pro
65                  70                  75                  80

Leu Leu Ile Ala Phe Glu Leu Leu Cys Ile Tyr Leu Glu Ser Leu
                85                  90                  95

Tyr Val Arg Gly Phe Pro Ala Val Asp Leu Lys Ile Val Phe Leu Pro
            100                 105                 110

Leu Leu Thr Phe Glu Val Ile Ile Leu Ile Asp Asn Phe Arg Met Cys
        115                 120                 125

Lys Ala Leu Met Pro Gly Asp Glu Glu Arg Met Ser Asp Glu Ala Ile
    130                 135                 140

Trp Glu Thr Leu Pro His Phe Trp Val Ala Ile Ser Met Val Phe Phe
145                 150                 155                 160

Val Ala Ala Thr Val Phe Thr Leu Leu Lys Leu Ser Gly Ser Val Ala
                165                 170                 175

Ser Leu Gly Trp Trp Asp Leu Phe Ile Asn Phe Thr Ile Ala Glu Cys
            180                 185                 190

Phe Ala Phe Leu Val Cys Thr Lys Trp Ser Asn Pro Val Ile His Arg
        195                 200                 205

Ser Ser Arg Glu Pro Ser Ser Ser Ser Thr Thr Ile Arg Tyr Leu
    210                 215                 220

Asp Trp Asn Asn Gly Leu Leu Val Ser Ser Glu Glu Asp Gln Arg Gln
225                 230                 235                 240

Ala Arg Ile Cys Thr Leu Gln Asp Ile Gly Gly His Phe Met Lys Val
                245                 250                 255

Pro Ile Ile Val Phe Gln Val Leu Leu Cys Met His Leu Glu Gly Thr
            260                 265                 270

Pro Ala Phe Ala Ala Gln Leu Pro Leu Ala Val Leu Phe Ser Pro Leu
        275                 280                 285

Phe Val Leu Gln Gly Val Gly Val Ile Leu Ser Ala Ser Lys Phe Val
    290                 295                 300

Glu Lys Leu Val Leu Leu Leu Arg Ser Gly Ala Gly Gly Gly Leu Tyr
```

```
                305                 310                 315                 320
Phe Arg Val Ser Ser Ile Ala His Asp Cys Leu Gly Phe Leu His His
                    325                 330                 335

Gly Ser Arg Leu Leu Gly Trp Trp Ser Ile Asp Glu Gly Ser Arg Glu
                340                 345                 350

Glu Gln Ala Arg Leu Tyr His Glu Gly Ala Ser Gly Tyr Asn Thr Phe
                355                 360                 365

Ser Gly Tyr Pro Pro Glu Ile Val Lys Lys Met Pro Lys Arg Asp Leu
            370                 375                 380

Ala Glu Glu Val Trp Arg Leu Gln Ala Ala Leu Gly Glu Gln Thr Glu
385                 390                 395                 400

Ile Thr Lys Tyr Ser Gln Gln Glu Tyr Glu Arg Leu Lys Asn Glu Lys
                405                 410                 415

Val Leu Cys Arg Ile Cys Phe Glu Gly Glu Ile Ser Val Val Leu Leu
                420                 425                 430

Pro Cys Arg His Arg Val Leu Cys Ser Leu Cys Ser Glu Lys Cys Lys
            435                 440                 445

Met Cys Pro Ile Cys Arg Asn Tyr Ile Ala Glu Arg Leu Pro Val Tyr
            450                 455                 460

Asp Val
465

<210> SEQ ID NO 48
<211> LENGTH: 468
<212> TYPE: PRT
<213> ORGANISM: Artificial Sequence
<220> FEATURE:
<223> OTHER INFORMATION: Synthetic construct
<220> FEATURE:
<221> NAME/KEY: Misc_feature
<222> LOCATION: (1)...(468)
<223> OTHER INFORMATION: Annotated protein NP_564945

<400> SEQUENCE: 48

Met Leu Val Gln Arg Arg Val Met Ser Trp Arg Arg Val Trp Lys Ser
1               5                   10                  15

Phe Gln Ala Ala Ser Ala His Cys Leu Leu Phe Ser Phe Thr Leu Leu
                20                  25                  30

Leu Ala Leu Lys Leu Asp His Val Ser His Ser Trp Trp Phe Val
            35                  40                  45

Phe Ala Pro Leu Trp Leu Phe His Ala Val Ile Ala Arg Gly Arg Phe
        50                  55                  60

Ser Leu Pro Ala Pro Ser Met Pro His Asp Arg His Trp Ala Pro Phe
65                  70                  75                  80

His Ser Val Met Ala Thr Pro Leu Leu Val Ala Phe Glu Ile Leu Leu
                85                  90                  95

Cys Val His Leu Glu Asp Lys Tyr Val Val Asp Leu Lys Ile Val Phe
                100                 105                 110

Leu Pro Leu Leu Ala Phe Glu Val Ala Ile Leu Ile Asp Asn Val Arg
            115                 120                 125

Met Cys Arg Thr Leu Met Pro Gly Asp Glu Glu Thr Met Ser Asp Glu
        130                 135                 140

Ala Ile Trp Glu Thr Leu Pro His Phe Trp Val Ser Ile Ser Met Val
145                 150                 155                 160

Phe Phe Ile Ala Ala Thr Thr Phe Thr Leu Leu Lys Leu Cys Gly Asp
                165                 170                 175

Val Ala Ala Leu Gly Trp Trp Asp Leu Phe Ile Asn Phe Gly Ile Ala
```

180                 185                 190
Glu Cys Phe Ala Phe Leu Val Cys Thr Lys Trp Ser Asn Gln Ser Ile
            195                 200                 205
His Arg Tyr Ser His Ile Pro Glu Pro Ser Ser Ser Met Val Val
        210                 215                 220
Arg Tyr Leu Asp Trp Asn Arg Gly Leu Val Val Thr Ala Asp Asp Glu
225                 230                 235                 240
His Gln Gln Ser Asn Arg Ile Cys Gly Leu Gln Asp Ile Gly Gly His
                245                 250                 255
Val Met Lys Ile Pro Phe Val Thr Phe Gln Ile Ile Leu Phe Met Arg
            260                 265                 270
Leu Glu Gly Thr Pro Ala Ser Ala Lys Asn Ile Pro Ile Leu Val Leu
        275                 280                 285
Phe Val Pro Leu Phe Leu Leu Gln Gly Ala Gly Val Leu Phe Ala Met
        290                 295                 300
Tyr Arg Leu Val Glu Lys Ser Val Leu Leu Ile Asn Ser Gly Ser Gly
305                 310                 315                 320
Ser Tyr Gly Arg Tyr Phe Thr Ala Thr Ser Ser Ala Arg Glu Phe Leu
                325                 330                 335
Gly Phe Phe Gln His Gly Ala Arg Leu Leu Gly Trp Trp Ser Ile Asp
            340                 345                 350
Glu Gly Ser Arg Glu Glu Gln Ala Arg Leu Tyr Ser Gly Glu Ala Thr
        355                 360                 365
Gly Tyr Asn Thr Phe Ser Pro Glu Val Val Lys Lys Met Pro Lys Ser
        370                 375                 380
Asp Leu Val Glu Glu Ile Trp Arg Leu Gln Ala Ala Leu Ser Glu Gln
385                 390                 395                 400
Thr Asp Ile Thr Ser Tyr Ser Gln Gln Glu Tyr Glu Arg Leu Gln Asn
                405                 410                 415
Glu Lys Ile Leu Cys Arg Val Cys Phe Glu Asp Pro Ile Asn Val Val
            420                 425                 430
Leu Leu Pro Cys Arg His His Val Leu Cys Ser Thr Cys Cys Glu Lys
        435                 440                 445
Cys Lys Lys Cys Pro Ile Cys Arg Val Leu Ile Glu Glu Arg Met Pro
    450                 455                 460
Val Tyr Asp Val
465

<210> SEQ ID NO 49
<211> LENGTH: 497
<212> TYPE: PRT
<213> ORGANISM: Artificial Sequence
<220> FEATURE:
<223> OTHER INFORMATION: Synthetic construct
<220> FEATURE:
<221> NAME/KEY: Misc_feature
<222> LOCATION: (1)...(497)
<223> OTHER INFORMATION: Annotated protein ABE90658

<400> SEQUENCE: 49

Met Leu Val Arg Arg Val Met Ser Trp Arg Arg Val Phe Lys Ser
1               5                   10                  15
Leu Gln Ala Met Leu Ala His Ala Phe Leu Phe Ser Phe Ser Leu Leu
            20                  25                  30
Leu Val Leu Lys Leu Asp Arg Phe Phe Leu Phe Ser Trp Trp Thr Val
        35                  40                  45
Phe Phe Pro Leu Trp Leu Phe His Val Val Ile Ala Arg Gly Arg Phe

```
                50                  55                  60
Ser Leu Pro Ala Pro Ser Met Pro His Gly Arg Gln Trp Ala Pro Cys
 65                  70                  75                  80

His Ser Val Ile Ala Thr Pro Leu Leu Val Ala Phe Glu Leu Leu Leu
                 85                  90                  95

Cys Ile His Leu Gly Ser Ser Tyr Val Val Asn Leu Lys Ile Val Phe
                100                 105                 110

Ile Pro Leu Ile Ala Phe Glu Leu Ala Ile Leu Ile Asp Asn Ile Arg
                115                 120                 125

Met Cys Arg Ala Leu Met Pro Gly Asp Glu Glu Asn Met Thr Asp Glu
                130                 135                 140

Ala Val Trp Glu Thr Leu Pro His Phe Trp Ile Ser Ile Ser Met Val
145                 150                 155                 160

Phe Phe Val Ala Ala Thr Val Phe Thr Leu Leu Lys Ile Cys Gly Asp
                165                 170                 175

Val Ala Ala Leu Gly Trp Trp Asp Leu Phe Ile Asn Tyr Gly Tyr Asn
                180                 185                 190

Gln Tyr Leu Leu Val Asp Cys Phe Lys His Phe Ile Leu Ile Leu Tyr
                195                 200                 205

Phe Phe His His Lys Leu Ile Leu Ser Phe Cys Ser Ile Ala Gln Cys
                210                 215                 220

Phe Ala Phe Leu Val Cys Thr Lys Trp His Asn Pro Thr Ile His Gly
225                 230                 235                 240

Asn Gly His Ile Thr Glu Pro Cys Ser Ser Asn Thr Val Arg Tyr
                245                 250                 255

Leu Glu Trp Ser Arg Glu Gly Ile Val Ile Ser Thr Glu Glu Asp Glu
                260                 265                 270

Gln Gln Asn Val Phe Cys Ser Leu Gln Asp Ile Gly His Ile Met
                275                 280                 285

Lys Ile Pro Phe Ile Ala Phe Gln Ile Leu Leu Phe Met His Leu Glu
                290                 295                 300

Gly Thr Pro Ser Gly Ala Lys Asp Ile Pro Ile Trp Val Ile Phe Ser
305                 310                 315                 320

Pro Leu Leu Leu Gln Gly Ala Gly Val Leu Phe Ala Ala Tyr Arg
                325                 330                 335

Leu Ile Glu Lys Ile Ile Leu Leu Tyr Asn Gly Asp Ile Pro Arg
                340                 345                 350

Ser Tyr Ser Ser Ile Ser Ser Lys Ser Arg Asp Cys Phe Gly Phe Phe
                355                 360                 365

Asn His Gly Ser Arg Leu Leu Gly Trp Trp Ser Ile Asp Glu Gly Ser
                370                 375                 380

Arg Glu Glu Glu Ala Arg Leu Phe Cys Ala Gly Ser Ser Gly Tyr Asn
385                 390                 395                 400

Thr Phe Ser Pro Asp Thr Val Lys Lys Met Pro Arg Gly Glu Leu Val
                405                 410                 415

Glu Glu Ile Trp Arg Leu Gln Ala Ala Leu Gly Glu Gln Thr Glu Val
                420                 425                 430

Thr Lys Tyr Ser Gln Glu Glu Tyr Glu Arg Leu Gln Asn Glu Lys Ile
                435                 440                 445

Leu Cys Arg Val Cys Phe Glu Glu Gln Ile Asn Val Val Leu Leu Pro
                450                 455                 460

Cys Lys His His Val Leu Cys Ser Thr Cys Cys Glu Lys Cys Lys Lys
465                 470                 475                 480
```

```
Cys Pro Ile Cys Arg Gly Thr Ile Glu Glu Arg Met Pro Ile Tyr Asp
                485                 490                 495
Val
```

<210> SEQ ID NO 50
<211> LENGTH: 498
<212> TYPE: PRT
<213> ORGANISM: Artificial Sequence
<220> FEATURE:
<223> OTHER INFORMATION: Synthetic construct
<220> FEATURE:
<221> NAME/KEY: Misc_feature
<222> LOCATION: (1)...(498)
<223> OTHER INFORMATION: Annotated protein AAF25982

<400> SEQUENCE: 50

```
Met Val Phe Phe Pro Leu Trp Ala Phe His Ala Val Ala Arg Gly
1               5                   10                  15

Arg Phe Ser Leu Pro Ala Pro Val Ala Pro Arg Asn Arg His Trp Ala
                20                  25                  30

Pro Cys His Ala Val Val Ala Thr Pro Leu Leu Val Ala Phe Glu Leu
            35                  40                  45

Leu Leu Cys Ile Tyr Leu Glu Ser Ser Tyr Ala Arg Trp Pro Pro Ala
50                  55                  60

Val Ser Leu Lys Ile Ala Phe Leu Pro Leu Leu Ala Phe Glu Leu Thr
65                  70                  75                  80

Ile Leu Val Asp Asn Leu Arg Met Cys Arg Ala Leu Met Pro Gly Asp
                85                  90                  95

Asp Asp Ser Ile Thr Asp Asp Ala Ile Trp Glu Ala Leu Pro Val Ser
            100                 105                 110

Pro Leu Leu Leu His Lys Ile Phe Glu Gly Leu Ser Leu Arg Leu Gly
        115                 120                 125

Lys Ile Asn Leu Leu Asn Met Asn Glu Asn Leu Ser Leu Ile Phe Gln
130                 135                 140

Leu His Asn Ser Gly Leu Arg Arg Glu Lys Thr Leu Thr Asn His Phe
145                 150                 155                 160

Trp Val Ala Ile Ser Met Val Phe Thr Leu Ala Ala Thr Phe Phe Thr
                165                 170                 175

Leu Leu Lys Leu Ser Val Phe Glu Lys Tyr Leu Pro Phe Leu Trp Leu
            180                 185                 190

Leu Val Lys Asn Met Lys Val Ile Tyr Met Lys Cys Ser Ala Cys Arg
        195                 200                 205

Ile Ala Glu Cys Phe Ala Phe Leu Val Cys Thr Lys Trp Ser Asn Pro
210                 215                 220

Val Ile His Arg Ser Ser Arg Ala Arg Glu Thr Gly Ser Ser Ser Thr
225                 230                 235                 240

Ser Ile Arg Tyr Leu Asp Trp Asn Ser Gly Leu Val Val Ala Pro Glu
                245                 250                 255

Glu Asp Arg His Gln Asp Arg Trp Cys Gly Leu Gln Asp Ile Gly Gly
            260                 265                 270

His Met Leu Lys Ile Pro Val Ile Leu Phe Gln Val Leu Cys Met
        275                 280                 285

Tyr Leu Glu Gly Thr Pro Glu Arg Ala Lys Asp Ile Ser Ile Pro Val
            290                 295                 300

Leu Phe Ser Pro Leu Phe Leu Leu Gln Gly Leu Gly Val Leu Phe Ala
305                 310                 315                 320

Ala Ser Lys Leu Leu Glu Lys Ile Val Leu Leu Leu Arg Gly Glu Ala
```

```
            325                 330                 335
Gly Pro Gly Leu Tyr Phe Arg Phe Ser Ser Ala His Asp Cys Leu
            340                 345                 350

Gly Phe Leu His His Gly Ser Arg Leu Leu Gly Trp Trp Ser Ile Asp
                355                 360                 365

Glu Gly Ser Arg Glu Glu Gln Ala Arg Leu Tyr Phe Asp Gln Glu Ser
            370                 375                 380

Gly Leu Val Trp Arg Leu Gln Ala Ala Leu Gly Glu Gln Thr Glu Ile
385                 390                 395                 400

Thr Lys Phe Ser Gln Gln Glu Tyr Glu Arg Leu Gln Asn Val Tyr Ser
                405                 410                 415

Phe Ile Ser His Asp Val Phe Val Thr Phe Leu Phe Arg Phe Tyr Phe
                420                 425                 430

Phe Pro Leu Leu Asn Pro Val Ser Met Cys Leu Leu Leu Gln Glu Lys
                435                 440                 445

Val Leu Cys Arg Val Cys Phe Glu Lys Asp Ile Ser Leu Val Leu Leu
            450                 455                 460

Pro Cys Arg His Arg Val Leu Cys Arg Thr Cys Ala Asp Lys Cys Thr
465                 470                 475                 480

Thr Cys Pro Ile Cys Arg Ile Asp Ile Glu Lys Arg Leu Ser Val Tyr
                485                 490                 495

Asp Val

<210> SEQ ID NO 51
<211> LENGTH: 354
<212> TYPE: DNA
<213> ORGANISM: Artificial Sequence
<220> FEATURE:
<223> OTHER INFORMATION: Synthetic construct
<220> FEATURE:
<221> NAME/KEY: Misc_feature
<222> LOCATION: (1)...(354)
<223> OTHER INFORMATION: OsRHC1 binding partner
<220> FEATURE:
<221> NAME/KEY: CDS
<222> LOCATION: (1)...(354)

<400> SEQUENCE: 51 atg gcc gtg ggg tca gag cgg ctc ggc gag gag gcc gcc cgg cgg cag      48
Met Ala Val Gly Ser Glu Arg Leu Gly Glu Glu Ala Ala Arg Arg Gln
1               5                   10                  15 ctc ggc gag gca agg aag gcc aga ggc ggc tgc tcg gcg acg agg gac      96
Leu Gly Glu Ala Arg Lys Ala Arg Gly Gly Cys Ser Ala Thr Arg Asp
                20                  25                  30 ggc gcc gat gat gag ggc cgg cgg cag ata aac cct ccc tcc ccg gtg     144
Gly Ala Asp Asp Glu Gly Arg Arg Gln Ile Asn Pro Pro Ser Pro Val
            35                  40                  45 tgg tcg tcc cct ccc tca ctc cct ctt cct ctc aga tct gcc cgg agg     192
Trp Ser Ser Pro Pro Ser Leu Pro Leu Pro Leu Arg Ser Ala Arg Arg
        50                  55                  60 ggg acg ggt gga ggc cgg cgg cct ccc ttc cct ctt tcc tct cag atc     240
Gly Thr Gly Gly Gly Arg Arg Pro Pro Phe Pro Leu Ser Ser Gln Ile
65                  70                  75                  80 cgc ccg gtg ggg aga ggc cac cgg cgg cag cgg cat ggc cct ccc ctc     288
Arg Pro Val Gly Arg Gly His Arg Arg Gln Arg His Gly Pro Pro Leu
                85                  90                  95 tgc agc agt aga ggg cgg cag gga gga ggc cac aga gct gtg ttt ttt     336
Cys Ser Ser Arg Gly Arg Gln Gly Gly Gly His Arg Ala Val Phe Phe
                100                 105                 110 tat ttg ttt tta ttt tga                                             354
```

-continued

```
Tyr Leu Phe Leu Phe
            115

<210> SEQ ID NO 52
<211> LENGTH: 117
<212> TYPE: PRT
<213> ORGANISM: Artificial Sequence
<220> FEATURE:
<223> OTHER INFORMATION: Synthetic construct
<220> FEATURE:
<221> NAME/KEY: Misc_feature
<222> LOCATION: (1)...(117)
<223> OTHER INFORMATION: OsRHC1 binding partner

<400> SEQUENCE: 52

Met Ala Val Gly Ser Glu Arg Leu Gly Glu Glu Ala Ala Arg Arg Gln
1               5                   10                  15

Leu Gly Glu Ala Arg Lys Ala Arg Gly Gly Cys Ser Ala Thr Arg Asp
            20                  25                  30

Gly Ala Asp Asp Glu Gly Arg Arg Gln Ile Asn Pro Pro Ser Pro Val
        35                  40                  45

Trp Ser Ser Pro Pro Ser Leu Pro Leu Pro Leu Arg Ser Ala Arg Arg
    50                  55                  60

Gly Thr Gly Gly Gly Arg Arg Pro Pro Phe Pro Leu Ser Ser Gln Ile
65                  70                  75                  80

Arg Pro Val Gly Arg Gly His Arg Arg Gln Arg His Gly Pro Pro Leu
                85                  90                  95

Cys Ser Ser Arg Gly Arg Gln Gly Gly Gly His Arg Ala Val Phe Phe
            100                 105                 110

Tyr Leu Phe Leu Phe
            115
```

METHOD TO IMPROVE PLANT RESISTANCE TO INFECTIONS

RELATED APPLICATIONS

This application claims priority from U.S. provisional applications 60/947,590 filed 2 Jul. 2007 and 60/947,365 filed 29 Jun. 2007. The contents of these applications are incorporated herein by reference in their entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 549072000700Seqlist.txt | Jul. 23, 2010 | 51,884 bytes |

TECHNICAL FIELD

The invention relates to proteins that improve the resistance of plants to infections, including infections by pathogen and wounding. The invention also concerns methods to improve the resistance of plants to infections by effecting expression of the genes encoding these proteins.

BACKGROUND ART

Preformed and induced defense mechanisms provide a wide spectrum of resistance toward numerous pathogens encountered by the plant host. Pathogen specific defense responses are usually initiated by the recognition of a pathogen avirulent (Avr) protein by the corresponding resistance (R) protein of the host. Ultimately, the plant host will produce a series of defense molecules (including pathogenesis-related proteins) to restrict or kill the pathogens. The processes between the initiation of resistance and the production of resistance proteins involve a complex signal transduction network which is yet to be fully elucidated.

In *Arabidopsis thaliana*, many important hubs of the defense signaling network have been identified by molecular genetic approaches, including EDS1 (Enhanced Disease Susceptibility 1), NPR1 (Non-Expresser of PR Genes 1) and NDR1 (Non Race-Specific Disease Resistance 1). Using similar tactics and together with biochemical studies, the involvement of phytohormone signals in defense responses has been corroborated in *A. thaliana*, especially the roles of salicylic acid (SA), and the other phytohormones such as jasmonic acid (JA) and ethylene (ET).

Many known signaling strategies are employed in plant defense responses. For instance, some R proteins are receptor kinases while other protein kinases also play significant roles. Biochemical signals such as calcium flux and oxidative burst are also important. Furthermore, there are several reports on the participation of other signaling components such as G-proteins and RING (Really Interesting New Gene) zinc finger proteins.

RING zinc finger proteins are a group of diverse proteins with highly conserved zinc binding domains. Based on the type of cysteine (C) and histidine (H) residue combination, the RING zinc finger domain can be classified into canonical and modified RING zinc fingers. The canonical RING zinc finger can be further grouped into two subclasses: HC subclass (consensus: C—$X_2$—C—$X_{9-39}$—C—$X_{1-3}$—H—$X_{2-3}$—C—$X_2$—C—$X_{4-48}$—C—$X_2$—C) (SEQ ID NO:1) and H2 subclass (consensus: C—$X_2$—C—$X_{9-39}$—C—$X_{1-3}$—H—$X_{2-3}$—H—$X_2$—C—$X_{4-48}$—C—$X_2$—C) (SEQ ID NO:2) (Stone, S. L., et al., *Plant Physiology* (2005) 137:13-30). Modified RING zinc fingers include RING-C2, RING-v, RING-D, RING-S/T and RING-G.

Many members of the RING zinc finger protein family (including both HC and H2 subclasses) are E3 ubiquitin ligases. Different subclasses of the RING zinc finger domain determine specificity toward different E2 ubiquitin conjugating enzymes. Other RING zinc finger proteins can bind to nucleic acids or interact with other protein targets. Besides the ubiquitin mediated degradation pathway, RING zinc finger proteins also play important roles in organelle transport and transcription/translation regulations.

In rice, more than 30 resistance loci (Xa loci) against the pathogen *Xanthomonas oryzae* pv. *oryzae* (Xoo) have been identified and 6 Xa genes were cloned mainly by map-based cloning approaches. Several pathogenesis-related (PR) genes have been reported to contribute directly to the resistance mechanism. However, only a few key components of the signal transduction pathway from the onset of R protein-Avr protein interaction to the actual resistance development have been studied. To obtain new signal transduction components related to Xoo resistance in rice, cDNA clones differentially expressed in rice lines harboring Xa loci were searched for.

The present inventors have cloned and characterized a novel RING zinc finger protein gene (OsRHC1) from rice. OsRHC1 is differentially expressed under wounding in near isogenic lines containing the Xa14 or Xa23 resistance loci, but not in the corresponding susceptible recurrent parents. Ectopic expression of OsRHC1 in transgenic *A. thaliana* enhances its resistance toward bacterial pathogens and such protective function depends on the action of the 26S proteasome.

DISCLOSURE OF THE INVENTION

A variety of genes encoding infection resistance proteins is known in plants, and various transgenic plants modified to produce them have been used in attempts to confer resistance to infections. However, these resistance proteins appear to have a limited spectrum of activity with respect to the types of pathogens that they will successfully recognize. Many cause negative side effects (such as programmed cell death) as well. The present invention provides materials that can be used to confer resistance to infections on a wide variety of plants, without apparent negative side effects. The invention provides recombinant materials for the production of a protein designated OsRHC1 which is a RING zinc finger protein that confers resistance to infections of a broad spectrum of pathogens. Because the protein of the invention which is derived from a monocot (rice) is also effective in dicots (*Arabidopsis*) it is applicable to a broad spectrum of plants as well.

In one aspect, the invention is directed to expression systems that produce the OsRHC1 protein and proteins closely related thereto that are RING zinc finger proteins and are able to improve resistance of plants to infections. Transgenic plants modified with the expression systems of the invention have enhanced ability to resist infections either from pathogenic organisms or by wounding.

Thus, in another aspect, the invention is directed to plant cells or plants that have been modified to contain an expression system that produces this RING zinc finger protein. The plants may either be heterologous from the origin of OsRHC1 or may be rice plants modified to overexpress this protein.

In still another aspect, the protein produced by this expression system may be used to conduct screening assays to identify compounds or combinations of compounds that modulate resistance to infections in plants.

The invention also relates to antibodies that are immunospecific for the OsRHC1 protein. These antibodies are useful for detecting and purifying this protein.

BRIEF DESCRIPTION OF THE DRAWINGS

FIG. 1 shows the nucleotide sequence-encoding region of the OsRHC1 gene and the amino acid sequence of the OsRHC1 protein (SEQ ID NOS:42-43).

FIG. 2A shows the full-length amino acid sequence of OsRHC1 (SEQ ID NO:43) aligned to seven annotated proteins (SEQ ID NOS:44-50) exhibiting high degree of similarity.

FIG. 4A is a graph showing wounding-induced expression of OsRHC1 by real-time PCR. FIG. 4B shows a Western blot of the corresponding protein.

FIGS. 5A-C show pathogen inoculation tests of transgenic *A. thaliana* expressing OsRHC1. The expression of the transgene OsRHC1 in the transgenic lines was confirmed by Northern blot analysis in FIG. 5A. The disease symptoms were visible as shown in FIG. 5B and the rosette leaves (not at the site of infection) were harvested to estimate the titer of pathogens shown in FIG. 5C.

FIGS. 7A-D are graphs showing expression of defense marker genes (PR1 (A), PR2 (B), PDF1.2 (C) and Thi2.1 (D)) when treated with MG132 (a 26S proteasome inhibitor).

FIG. 8A shows the expression of the OsRHC1 gene and FIG. 8B shows the expression of four defense marker genes.

FIG. 9 shows the results of PCR screening of the OsRHC1 transgene in transgenic rice lines.

FIG. 10A shows the expression of OsRHC1 by real-time PCR and FIG. 10B shows production of the corresponding protein in transgenic rice lines.

FIG. 12 shows the results of autoubiquitination assay conducted on the RING-HC-C-terminal portion of OsRHC1.

FIG. 13 shows the DNA sequence (SEQ ID NO:51) and deduced amino acid sequence (SEQ ID NO:52) of a binding partner for OsRHC1.

MODES OF CARRYING OUT THE INVENTION

Figure 2B:
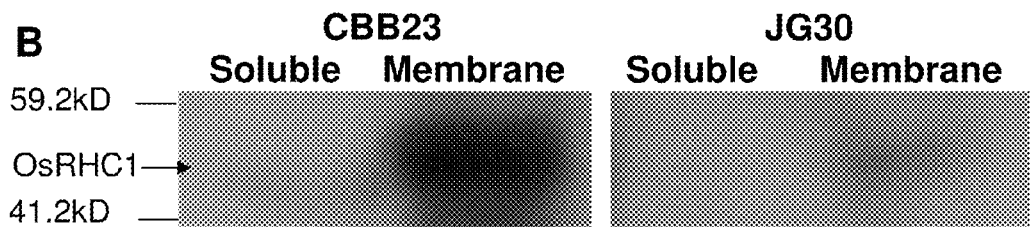
FIG. 2B shows membrane bound and soluble protein fractions extracted from CBB23 and JG30 followed by Western blot analysis using anti-OsRHC1 antibodies.

A protein designated rice RING-HC subclass protein-1 (OsRHC1) is a 409-amino acid protein overexpressed in rice in response to pathogen or wound-induced infections. This protein and its variants, which share at least 90%, preferably 95%, more preferably 98% or 99% sequence identity over the entire length of this 409-amino acid sequence (shown in FIG. 1) are able to confer resistance to the negative effects of infection to a wide variety of plants when said plants are modified to produce these proteins (collectively referred to as OsRHC1 proteins). The present invention provides expression systems that can be used to modify a wide variety of plants, both monocots and dicots, to enhance their ability to resist infections. The generic capability of such expression systems to confer resistance is confirmed in the examples hereinbelow which demonstrate that the protein, which has its origin in the monocot, rice, is able to confer these properties on the dicot *A. thaliana*.

The techniques for constructing expression vectors operable in plants, for modifying plant cells, for regenerating plant cells into intact plants and recombinant manipulation of plants in general are by this time well known. A summary of such techniques is found, for example, in U.S. Pat. No. 7,109,033 which is incorporated herein by reference for its disclosure of these techniques.

As noted in this patent, promoters useful in plant expression may be constitutive, inducible and/or tissue-specific. Transformation techniques include use of *Agrobacterium*, lipofection, electroporation, and the like. Techniques for regeneration of plants from transformed plant cells are also well established.

Accordingly, once the nucleotide sequence encoding the OsRHC1 protein is available, methods of preparing transgenic plants that produce these proteins are well within the ordinary skill of the art. The nucleotide sequence natively producing this protein has been deposited in GenBank with Accession No. EF584506 and synthetic alternatives having variations in codon usage are possible.

Thus, according to the invention, a suitable expression system is constructed for operability in plants wherein the nucleotide sequence encoding the proteins of the invention is operably linked to suitable control sequences operable in plants. This expression system is used to modify plant cells or plants so that the protein is produced either ubiquitously in plant tissues or in specialized desired locations in the plant, depending on the choice of control system and method of transformation. The resulting plants, whether monocots or dicots, are then permitted to produce the protein in response to pathogen or wound-induced infection so as to enhance their ability to resist damage caused by these infectious events.

As shown below, OsRHC1 is an E3 ubiquitin ligase which enhances the destruction of unwanted proteins by directing them to the proteasome. This property is shared in common with other RING proteins, and represents one aspect of its protective function. This protein is the first E3 that harbors transmembrane domains at the N-terminal region and RING-HC at the C-terminal cytoplasmic tail that has been found to be involved in plant disease resistance.

In addition, the protein itself, produced in sufficient quantity and isolated and purified to a suitable extent (at least 50% pure by weight, preferably 75% pure, more preferably 90% or 95% pure) can be used as a screening tool. Compounds or combinations of compounds that are able to bind the protein are candidates for modulating the ability of plants to resist infection. Compounds or combinations of compounds that, by binding the protein, are able to agonize its activity will enhance the infection-resisting capability of plants that are able to produce this protein.

Thus, the binding assay may be used as a preliminary screen. As it has been shown that OsRHC1 is an E3 ubiquitin ligase, the assay for ubiquitin ligase activity described below in Example 9, or a similar assay for such activity is used to demonstrate the agonist activity of a candidate compound. Thus, a suitable candidate will enhance the ability of OsRHC1 to effect ubiquitination.

Also useful for purifying the proteins of the invention and for detecting them are antibodies that are specifically immunoreactive with said proteins. The term "antibodies" is understood to mean complete antibodies, polyclonal or monoclonal, as well as the immunospecific fragments thereof such as Fab fragments, as well as recombinantly produced forms such as single-chain $F_v$ antibodies. Thus, the term "antibodies" refers both to any form of the antibody and to any portion thereof that retains its immunospecific characteristics. Such antibodies can be used, for example, on affinity columns, etc., for purification.

In the examples below, the nucleotide sequence encoding the OsRHC1 protein shown in FIG. 1 has been retrieved from rice and deposited. Further, it was demonstrated that the OsRHC1 expression, both at an mRNA level and at a protein level, could be induced in a line of rice that exhibits resistance in response to a pathogen and in response to wounding.

Transgenic *A. thaliana* plants were obtained using an expression construct for the OsRHC1 protein, and these transgenic plants were shown to have enhanced expression of four defense marker genes, both under regular growth conditions and when salicylic acid or jasmonic acid was added. The OsRHC1 transgenic *A. thaliana* also showed constitutive expression of the OsRHC1-encoding DNA and was protected by this expression when challenged with a *Pseudomonas*. Similarly, overexpression of this DNA in rice resulted in expression of several defense marker genes.

The following examples are offered to illustrate but not to limit the invention.

EXAMPLE 1

Identification and Cloning of OsRHC1-Encoding cDNA

One partial cDNA clone was obtained via suppression subtractive hybridization techniques with the PCR-select cDNA subtraction kit (Clontech 637401), using total RNA extracted from six to eight-week-old CBB14 which is bacterial blight resistant (tester) and SN1033 the susceptible parent of CBB14 (driver) rice lines collected four days after pathogen (Xoo race LN44) inoculation. Inoculation was performed by clipping method described in Zhang, Q., et al., *Acta Agr. Sin.* (1996) 22:135-141. Using the DNA sequence information of this partial clone, 5'-Rapid-Amplification of cDNA Ends (5'-RACE) experiment and subsequent PCR amplifications using specific primers were performed. Gene specific primers 5'-TTCTCC ATGTTCGGTAAACCTTTC-3' (SEQ ID NO:3), 5'-TAAAGTTGTGATTGAGACTACA TGG-3' (SEQ ID NO:4) and 5'-ACATTGCACAACCAACATGTAC-3' (SEQ ID NO:5) were employed in the 5'RACE reactions. To amplify the full length coding region, PCR using the primer pair 5'-CCTCACTTTTGTCTCCCAC-3' (SEQ ID NO:6) and 5'-CGACATTGCACA ACCAAC-3' (SEQ ID NO:7) were performed. All clones were stored in the plasmid vector pBluescript® KSII(+) (Stratagene) and propagated in the *E. coli* strain DH5α.

The resulting cDNA clone (GenBank accession number EF584506) encodes an intact open reading frame of 409 amino acid residues (FIG. 1). EF584506 is 99% identical to a directly deposited rice cDNA clone (accession number: NM_001057564). The corresponding gene in the rice genome appears to be a single copy gene located on chromosome 3. BlastP search showed that the protein encoded by our clone exhibits 99% identity to a rice clone annotated as a zinc finger family protein (accession number: ABF98464), but missing 64 amino acid residues at the N-terminus. Further analysis using the conserved domain database (CDD) revealed that the predicted protein harbors a RING zinc finger domain. The pattern of the conserved cysteine and histidine residues in the RING zinc finger domain exhibited a signature for the RING-HC subclass. The clone was designated as OsRHC1 accordingly.

The predicted amino acid sequence of the OsRHC1 protein was compared with two RING zinc finger proteins, EL5 (RING-H2 subclass) and XB3 (RING-HC subclass) from rice that are involved in disease resistance. No significant homology was found except at the RING zinc finger domain (data not shown). The RING zinc finger domain of OsRHC1 is located at the C-terminus (FIG. 2A) while such domain in EL5 and XB3 is located in the middle portion or close to the C-terminus of the protein, respectively. Prediction by the TopPred and the iPSORT programs suggested that OsRHC1 may possess multiple transmembrane domains (FIG. 2A) while EL5 only has one and XB3 does not possess any transmembrane region with high certainty (data not shown).

BlastP analysis revealed that OsRHC1 shares high amino acid sequence homology to seven other annotated proteins deposited in GenBank from various plant species (FIG. 2A). These proteins exhibit greater than 50% identity (spanning full length) to OsRHC1, with multiple transmembrane domains at the N terminal half, and a RING-HC domain at the C-terminus. The consensus of the RING-HC domain for this group of proteins is Cys-$X_2$-Cys-$X_{11}$-Cys-X-His-$X_3$-Cys-$X_2$-Cys-$X_6$-Cys-$X_2$-Cys (SEQ ID NO:8). There is apparently no published information on the functions of these homologues.

EXAMPLE 2

Demonstration that OsRHC1 is Membrane Bound

To verify that the OsRHC1 is membrane bound as depicted by bioinformatics tools, membrane-bound and soluble proteins were separated using a fractionation protocol (modified from Jiang and Rogers, *J. Cell Biol.* (1998) 143:1183-1199). For Western blot analysis, the proteins were electrophoretically separated on a polyacrylamide gel (4% stacking; 10% resolving) before transferred to an activated PVDF membrane (pre-treated in absolute methanol for 20 minutes followed by protein transfer buffer for 15 minutes) using the Trans-Blot® SD Semi-Dry Electrophoretic Transfer Cell (Bio-Rad 170-3949). The blocking and detection steps were performed according to the manufacturer's manual (Western Breeze™ Immunodetection Kit, InvitroGen WB7106). Primary antibodies (polyclonal) targeting the OsRHC1 protein was raised by a commercial service (InvitroGen, Custom antibody) via injecting a synthetic peptide ('N'-CGYPPEV-VRKMPKRD-'C') (SEQ ID NO:9) into rabbits and antibodies were purified using affinity column before use. Anti-rabbit secondary antibody conjugated to an alkaline phosphatase (provided in Western Breeze™ Immunodetection Kit, InvitroGen WB7106) was used to recognize the primary antibodies. Western blot analysis confirmed that the OsRHC1 protein was tightly associated to membranes (FIG. 2B).

EXAMPLE 3

OsRHC1 is Wound-Inducible in the Rice Lines CBB14 and CBB23

To study the expression pattern of OsRHC1, real-time PCR analyses was performed using reverse-transcribed RNA samples from two near isogenic pairs (CBB14 containing Xa14 and its susceptible recurrent parent SN1033; CBB23 a resistant line containing Xa23 and its susceptible recurrent parent JG30). Rice lines were grown on regular field soil in a green house (temperature 24-28° C.; RH 70-80%; under natural light). Inoculation of the Xoo races LN44 and P6 was performed by clipping method described in Zhang, Q., et al., supra (1996). Mock inoculation and wounding treatment followed the same procedure except that the pathogen was replaced by water. For the time-course experiments, samples were collected at 0, 2, 4, 6 days at around the same time of the day (between 8-10 am). Day 0 sample was collected before treatment.

For evaluating expression of OsRHC1 via real-time PCR, total RNA was extracted by the phenol extraction method of Ausubel, et al., *Current Protocols in Molecular Biology* (1995) J. Wiley & Sons, New York. The cDNA samples were generated by reverse transcription (18-mer oligo-dT; SUPERSCRIPT™ II RNaseH (InvitroGen 18064-071)) of DNase I (InvitroGen 18068-015)-treated RNA samples.

Real-time PCR amplification of cDNA was conducted using the ABI PRISM 7700 Sequence Detection System (Applied Biosystems) in 96-wells PCR plate with dome cap. Reaction was carried out in a 20 µl reaction volume containing 10 µl SYBR Green PCR Master Mix (Applied Biosystems 4309155) with 0.3 µM each of the forward and reverse primers. OsRHC1 primers for real-time PCR were 5'-AAAGAA-GAGCAAGCCCGGTTAT-3' (SEQ ID NO:10) and 5'-GC-CTCCATACCTCTTCTGCAA-3' (SEQ ID NO:11). All reactions were set independently for at least four times and at least three sets of consistent data were used for analysis. The expression level of actin (*O. sativa* OsAc1D; accession number: X15865) with the primer set 5'-CTTCATAGGAATG-GAAGCTGCGGGTA-3' (SEQ ID NO:12) and 5'-GACCAC-CTTGATCTTCATGCTGCTA-3' (SEQ ID NO:13) was used to normalize the results. The relative gene expression was calculated using the $2^{-\Delta\Delta C_T}$ method of Livak and Schmittgen, *Methods* (2001) 25:402-408.

To validate the reliability data, amplification efficiencies between the target genes and the housekeeping genes of all the real-time PCR reactions were compared, and dissociation curves of all PCR products were examined to ensure the quality of PCR. At least two independent batches of plant samples were used and gene expression patterns were consistently observed. All PCR products were sequenced at least one time to verify that the right targets were being quantified.

Figure 3:
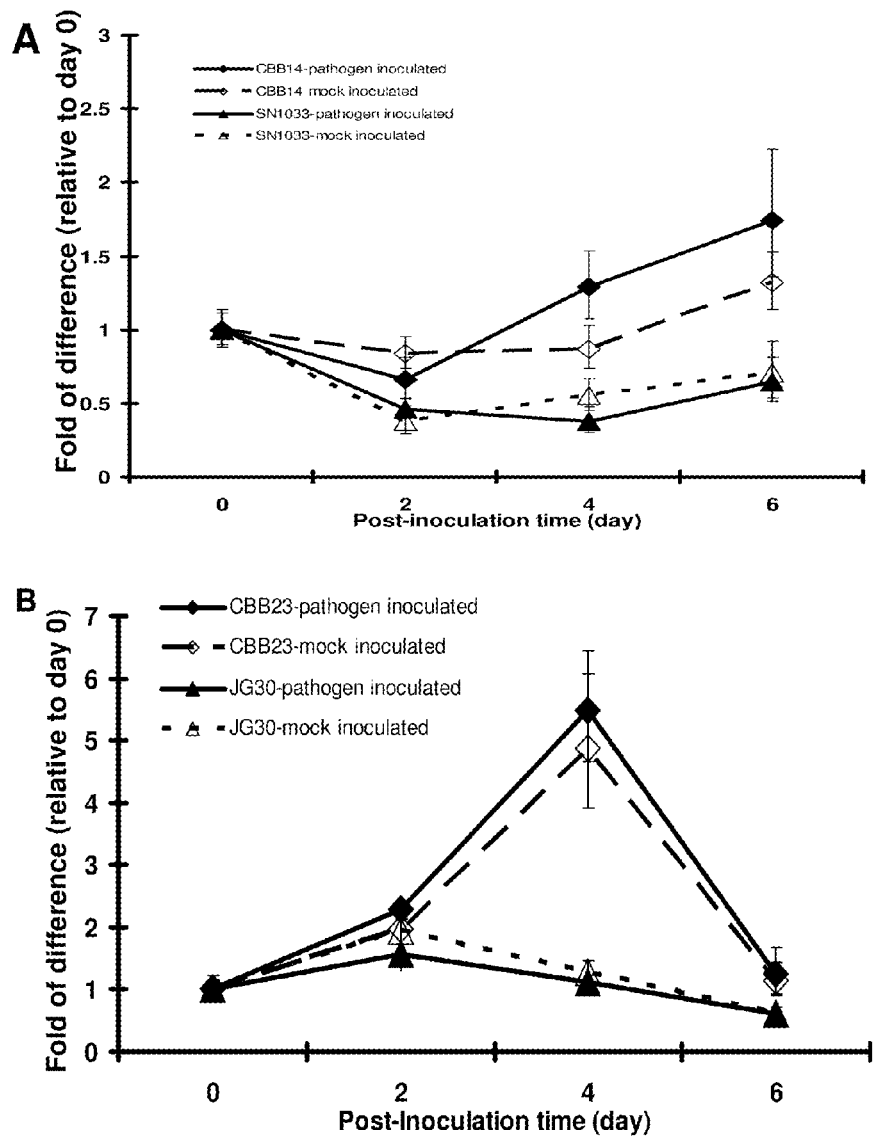
FIGS. 3A and 3B are graphs showing expression of OsRHC1 in bacterial blight resistant lines CBB14 and CBB23 (carrying the Xa14 locus and Xa23 locus, respectively) and their susceptible recurrent parents (SN1033 and JG30, respectively).

When an incompatible Xoo strain (LN44 for Xa14 and P6 for Xa23) was inoculated, the rice lines containing Xa14 or Xa23 exhibited an induction of OsRHC1 gene expression while the susceptible recurrent parents were non-responsive as shown in FIGS. 3A and 3B, respectively. However, such induction was also observed in mock inoculated samples which had been wounded, suggesting that OsRHC1 could be wounding-inducible. The amplitude of induction was much stronger in the case of CBB23 which harbors the Xa23 locus that confers broad spectrum resistance.

The effect of wounding on OsRHC1 expression in CBB23 line and its susceptible recurrent parent JG30 was further analyzed. Both RNA and protein samples were collected after wounding by leaf clipping. CBB23 and JG30 rice lines (eight-week-old plants) were wounded by clipping. Day 0 leaf samples were collected before wounding. Leaf tissues about 6-8 mm away from the wounding site were collected at 2, 4, and 6 days after clipping. Total RNA and membrane bound protein samples were prepared in parallel. Real-time PCR experiments were performed as described above. Western blot analysis was performed using the anti-OsRHC1 antibody as described in Example 2.

The induction peak of OsRHC1 gene expression appeared on Day 4 after treatment in CBB23 (FIG. 4A). Western blot analysis of membrane-bound proteins showed that the production of the OsRHC1 protein in CBB23 was greatly enhanced on Day 6 (FIG. 4B), after the induction of gene expression on Day 4. The response in JG30 was not obvious when compared to CBB23, indicating that the presence of the Xa23 locus may play a role in the wounding induction of OsRHC1.

EXAMPLE 4

Production of Transgenic *Arabidopsis* Lines

To test whether OsRHC1 could mediate resistance in dicots, an *A. thaliana* was modified to produce OsRHC1 protein and challenged with *Pseudomonas syringae* pv *tomato* DC3000. OsRHC1 cDNA was inserted into a binary vector and the transgene expression was driven by the Cauliflower Mosaic Virus 35S promoter. *Agrobacterium*-mediated transformation of the wildtype Col-0 *A. thaliana* line was performed using a vacuum infiltration method (Bechtold, N., et al., *Methods Mol. Biol.* (1998) 82:259-266). Transgenic plants with single insertion locus were screened by kanamycin resistance phenotype (encoded by the selection marker gene in the binary vector) of offspring. A 3:1 (resistant:sensitive) ratio verified by Chi-Square test in the T1 generation suggested a single insertion event.

Only positive transformants containing a single insertion locus were propagated to obtain homozygous lines for further experiments. The transgene expression in three independent homozygous transgenic lines was examined by Northern blot analysis. As shown in FIG. 5A, three transformed lines, B-1-4, G-1-5, and H-2-9, showed high levels of production of mRNA. However, the Col-0 line, the wildtype, showed no production of the mRNA.

*A. thaliana* was grown in a growth chamber (temperature 22-24° C.; RH 70-80%; light intensity 80-120 µE of a 16 h light-8 h dark cycle). The preparation of the Pst DC3000 culture, inoculation (by a dipping method), and subsequent titering were performed as previously described (modified from Kim, H. S., et al., *Plant Cell* (2002) 14:1469-1482; Uknes, S., et al., *Plant Cell* (1992) 4:645-656). Six-week-old seedlings were challenged with Pst DC3000 in a concentration of $10^8$ colony forming unit/ml in 10 mM $MgSO_4$ supplemented with 0.02% (v/v) Silwet L-77 (Pieterse, C. M. J., et al., *Plant Cell* (1998) 10:1571-1580; Ton, J., et al., *Mol. Plant-Microbe Interact.* (2002) 15:27-34).

Figure 5B:
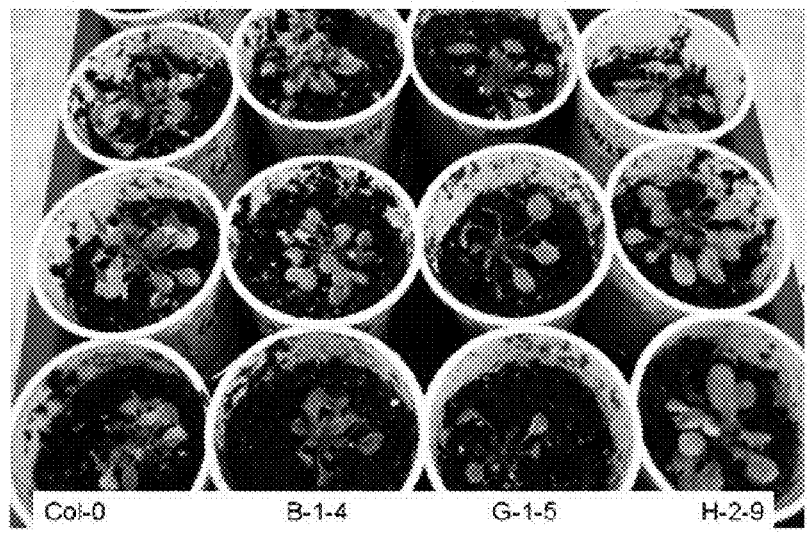

Pst DC3000 inoculation caused severe yellowing and necrosis in infected Col-0 and transgenic plants transformed with the empty vector V7, while the disease symptoms were much reduced in all OsRHC1 transgenic lines as shown in FIG. 5B.

Figure 5C:
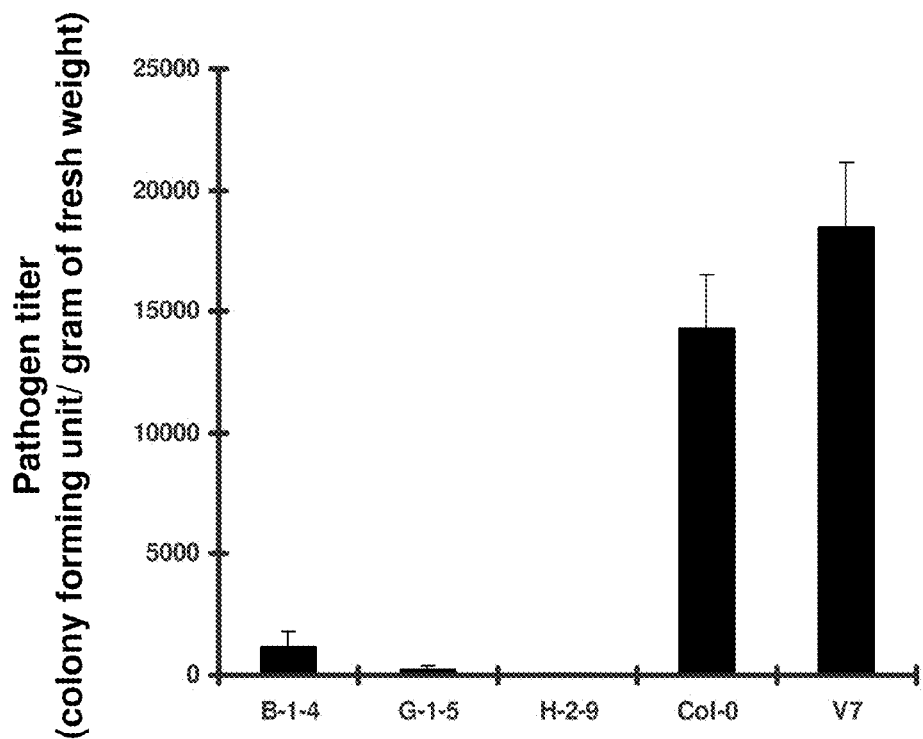

The titers of pathogen inside the rosette leaves were consistent with the observed phenotypes (FIG. 5C). Furthermore, the H-2-9 line that exhibited the highest level of transgene expression also gave the lowest pathogen titer (comparing FIGS. 5A and 5C).

EXAMPLE 5

Expression of OsRHC1 Enhances the Expression of Defense Marker Genes in Transgenic *Arabidopsis thaliana*

The expression of four defense marker genes, PR1, PR2, PDF1.2 and Thi2.1, was tested in transgenic *A. thaliana*. In *A. thaliana*, these genes are indicators of defense pathways mediated by different phytohormones including SA, JA, and ET.

Leaf tissues of six-week-old *A. thaliana* transgenic lines (B-1-4, G-1-5 and H-2-9) expressing OsRHC1 and the untransformed wild-type (Col-0) were harvested to prepare total RNA, followed by real-time PCR as described in Example 3. The primers used are as follows:

```
PR1:
5'-TCAAGATAGCCCACAAGATTATC-3'        (SEQ ID NO: 14)
and

5'-CTTCTCGTTCACATAATTCCCAC-3';       (SEQ ID NO: 15)

PR2:
5'-ACCACCACTGATACGTCTCCTC-3'         (SEQ ID NO: 16)
and

5'-AACTTCATACTTAGACTGTCGATC-3';      (SEQ ID NO: 17)

PDF1.2:
5'-CCCTTATCTTCGCTGCTCTTGT-3'         (SEQ ID NO: 18)
and

5'-CCCTGACCATGTCCCACTTG-3';          (SEQ ID NO: 19)

Thi2.1:
5'-AGCACTGCAAGTTAGGGTGTGA-3'         (SEQ ID NO: 20)
and

5'-ACATTGTTCCGACGCTCCAT-3'.          (SEQ ID NO: 21)
```

The tubulin (*A. thaliana*β-tubulin 4, accession number: M21415) with the primer set 5'-GAAGGTGCTGAGTTGATTG-3' (SEQ ID NO:22) and 5'-GGACTTGACGTTGTTTGG-3' (SEQ ID NO:23) was used to normalize the results.

Figure 6:
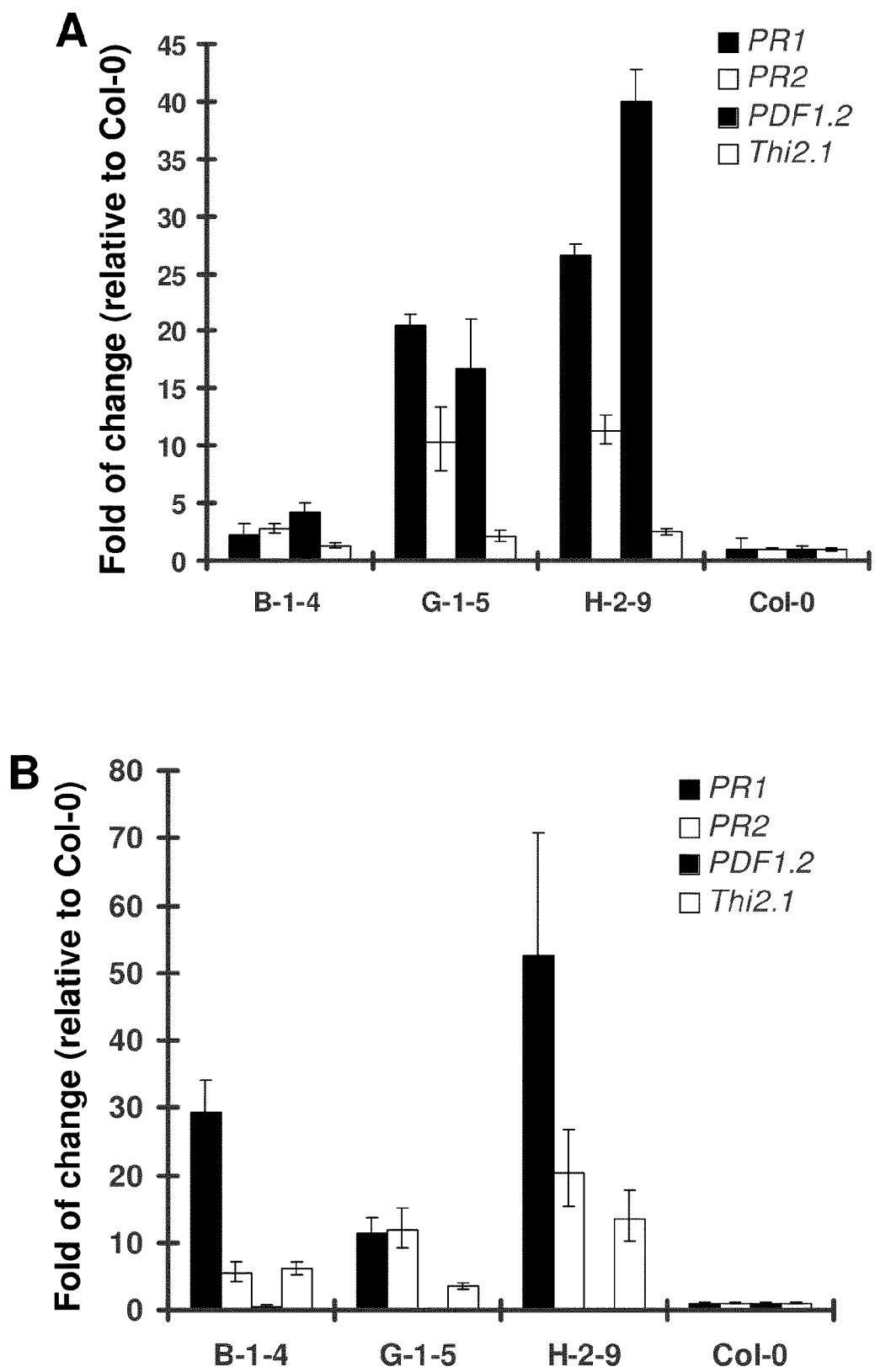
FIGS. 6A and 6B show expression of defense marker genes in transgenic *Arabidopsis thaliana* without (A) and with (B) *Pseudomonas syringae* pv. *tomato* DC3000 (Pst DC3000) inoculation.

The expressions of PR1 (solid), PR2 (open), PDF1.2 (hatched), and Thi2.1 (dotted) in each transgenic line as shown in FIG. 6A were compared to those of Col-0 (expression level set to 1).

In six-week-old seedlings under regular growth conditions, all four defense marker genes exhibited enhanced expression when compared to the wild type Col-0 (FIG. 6A). The fold of induction was particularly higher for the PR1 and the PDF1.2 genes which are mediated by two different signaling pathways. Among three independent transgenic lines tested, the H-2-9 line that showed highest expression of the transgene and best protection in the pathogen inoculation experiment also gave the highest fold of induction of PR1 and PDF1.2 (comparing FIGS. 5 and 6A).

When the plants were subjected to the challenge of Pst DC3000, the levels of PR1 and PR2 transcripts in Col-0 increased (data not shown) but the expression levels of these genes were even higher in transgenic lines (FIG. 6B). While the level of Thi2.1 in Col-0 did not alter significantly by the pathogen inoculation (data not shown), its expression was elevated in the transgenic lines (FIG. 6B). The expression of PDF1.2, on the other hand, was repressed by Pst DC3000 inoculation in both Col-0 and transgenic lines (FIG. 6B).

To show the relationship between the function of OsRHC1 and ubiquitin-mediated protein degradation, the effects of MG132 (a 26S proteasome inhibitor) on the expression of defense marker genes were studied in the transgenic lines. Four-week-old seedlings were subjected to MG132 treatment. The 26S proteasome inhibitor (MG132) was applied to the transgenic *A. thaliana* using a protocol modified from previous reports (Abas, L., et al., *Nature Cell Biol.* (2006) 8:249-256; Dong, C. H., et al., *Proc. Nat'l Acad. Sci. USA* (2006) 103:8281-8286; Guo, H., et al., *Cell* (2003) 115:667-677; Oñate-Sánchez, L., et al., *Plant Physiol.* (2002) 128: 1313-1322). In brief, 50 mg/L MG132 dissolved in 1% (v/v) DMSO supplemented with 0.01% (v/v) Silwet L-77 were poured onto MS square plates to cover the roots but not the aerial tissues of the seedlings. Mock treatment was performed with the same procedures except that no MG132 was added. After four hours, the seedlings were harvested for RNA extraction followed by real-time PCR.

Expression of the transgene was not affected by such treatment (data not shown). In Col-0, no significant effects of MG132 on the expression of defense marker genes were observed. On the other hand, the induction effects of overexpressing OsRHC1 on the four defense marker genes were diminished under MG132 treatment, as shown in FIGS. 7A-7D for PR1, PR2, PDF1.2, and Thi2.1, respectively, where open bars represent mock treatment and solid bars represent MG132 treatment In summary, it appears that the ability of the OsRHC1 protein to enhance the expression of the defense marker genes was, in all cases, inhibited by an inhibitor of the 26S proteasome. It thus appears that the ability of the invention protein to enhance expression of the defense marker genes may be dependent on the 26S proteasomal activity.

EXAMPLE 6

The Protective Function of the OsRHC1 Clone in Transgenic *Arabidopsis thaliana* is Dependent on the Function of NPR1

The function of OsRHC1 in relation to a known hub in the defense signaling network was positioned using the model plant system. NPR1 which mediates both SA and JA/ET signals and plays a central role in defense signaling in *A. thaliana*. OsRHC1 was transformed as described above into the npr1-3 *A. thaliana* mutant that is depleted of NPR1. Independent transformants with a single insertion locus were selected. At the time of inoculation, the expression of transgene (under the control of the Cauliflower Mosaic Virus 35S promoter) in individual lines was examined with real-time PCR as described in Example 3. The steady-state level of OsRHC1 in an npr1-3 background was found to be comparable to that in the transgenic lines with a Col-0 background (data not shown).

Figure 8:
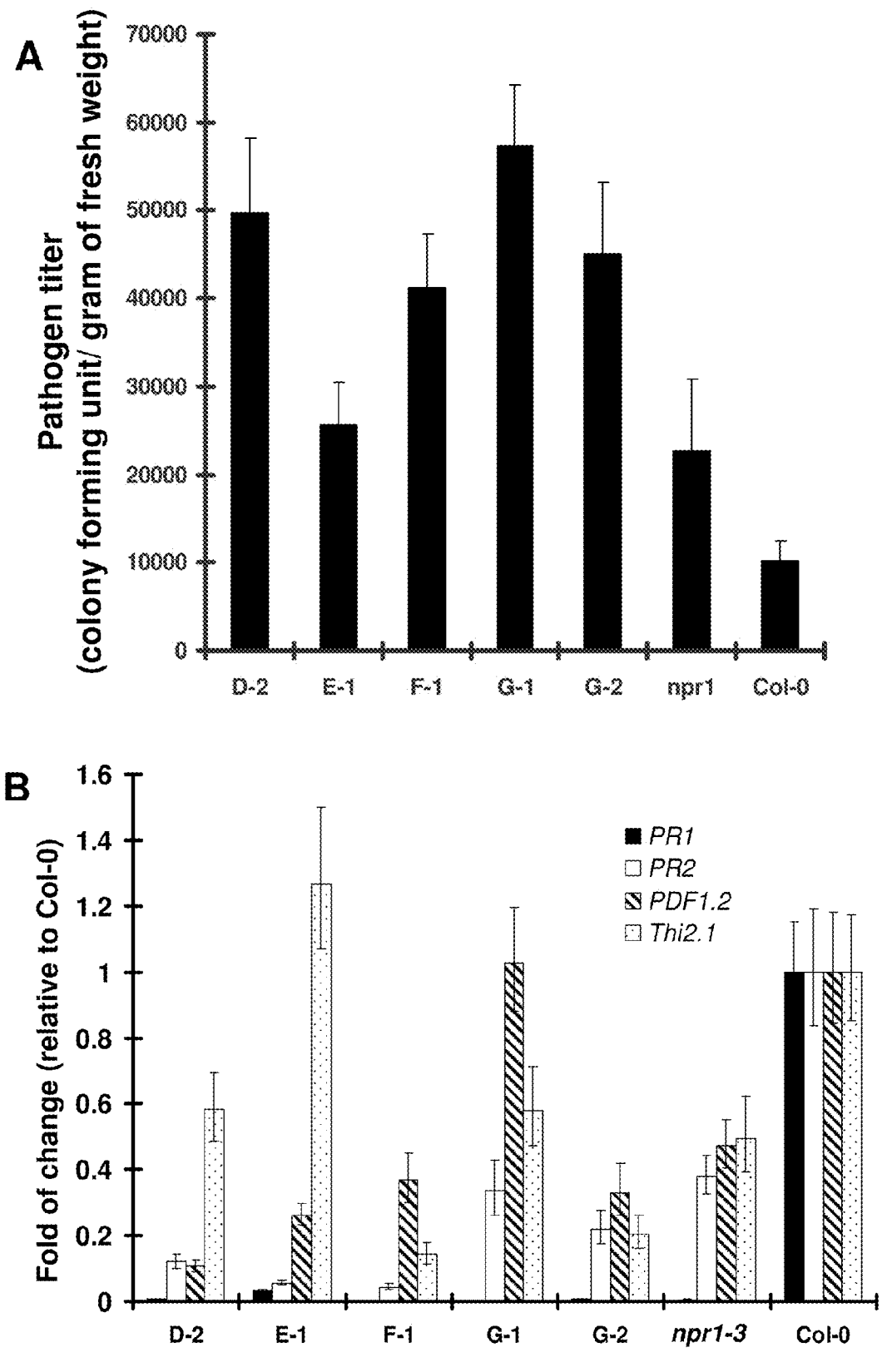
FIGS. 8A and 8B show the results of pathogen inoculation test of OsRHC1 transgenic *A. thaliana* in the npr1-3 background.

Eight-week-old transgenic lines (D-2, E-1, F-1, G-1 and G-2) expressing OsRHC1, the untransformed npr1-3 mutant, and the wild-type Col-0 were challenged by Pst DC3000 and the subsequent estimation of pathogen titer was obtained as shown in FIG. 8A. Expression of defense marker genes was determined as described in Example 5. The expressions of PR1 (solid), PR2 (open), PDF1.2 (hatched), and Thi2.1 (dotted) in each line was compared to those of Col-0 (expression level set to 1), as shown in FIG. 8B. No significant increase in the expression of four selected defense marker genes was found in any of these transgenic lines.

When the npr1-3 transgenic lines were subjected to the challenge of Pst DC3000, no protection effects could be observed in the transgenic lines. Both the disease symptom development (data not shown) and pathogen titer of these transgenic lines resembled that of the untransformed npr1-3 mutant. Thus, protection appears to require NPR1.

EXAMPLE 7

Construction of OsRHC1 Transgenic Rice

The nucleotide sequence of FIG. 1 encoding OsRHC1 was subcloned into a double T-DNA binary vector, pSB130 (from Dr. Liu Qiaoquan and Prof. Samuel Sun at the Chinese University of Hong Kong). The vector pSB130 carries two T-DNA. One T-DNA harbors the hygromycin resistance gene (selectable marker) and the other possesses a multiple cloning site downstream from a maize ubiquitin promoter for cloning of target genes. The recombinant construct was transformed into the *Agrobacterium* EHA105 for rice transformation, and transgenic rice lines were constructed.

FIG. 9 shows PCR screening of the OsRHC1 transgenes in T2 transgenic rice lines (parent: Aichi Asahi). The forward and reverse primers for PCR are from the maize ubiquitin promoter and the OsRHC1 coding region respectively as follows:

```
Forward primer:
5'-CTGATGCATATACATGATGG-3';          (SEQ ID NO: 24)

Reverse primer:
5'-ACATTGCACAACCAACATGTAC-3'.        (SEQ ID NO: 25)
```

A total of five OsRHC1 transgenic rice lines were obtained.

EXAMPLE 8

Over-Expression of OsRHC1 and Defense Marker Genes in Rice

The expression of the OsRHC1 and three rice defense marker genes (PR1, glycine rich cell wall protein encoding gene (GRCWP) and PBZ1) was studied via real-time PCR as described in Example 3. PR1 is a well known PR protein. Glycine rich cell wall protein (encoded by GRCWP) is a structural protein commonly found in strengthened cell wall to hinder pathogen attacks. PBZ1 is induced by probenazole (PBZ), N-cyanomethyl-2-chloro-isonicotinamide (compounds known to induce disease resistance) as well as the fungal blast pathogen *M. grisea*. PBZ1 is induced faster by incompatible strains of *M. grisea* than compatible strains. PR1 and PBZ1 are induced by over-expression of NH1, a key signaling component in rice defense response.

The RNA was extracted from 8-week-old plants of the transgenic rice lines (at the T3 generation) carrying a single insertion of OsRHC1 and their wild type parent (Aichi Asahi). The primers used in real-time PCR are as follows:

```
O. sativa OsRHC1 forward primer:
5'-AAAGAAGAGCAAGCCCGGTTAT-3';        (SEQ ID NO: 26)

O. sativa OsRHC1 reverse primer:
5'-GCCTCCATACCTCTTCTGCAA-3';         (SEQ ID NO: 27)

O. sativa PR1 (BF889437) forward primer:
5'-CGGACAGAGGCCTTACTAAGTTATTT-3';    (SEQ ID NO: 28)

O. sativa PR1 (BF889437) reverse primer:
                                     (SEQ ID NO: 29)
5'-GACCTGTTTACATTTTCACGTCTTTATT-3';
```

```
O. sativa GRCWP (BF889438) forward primer:
5'-GAGGCAACGGACACCACTAAG-3';         (SEQ ID NO: 30)

O. sativa GRCWP (BF889438) reverse primer:
5'-TGTAAAGCAGAGAGAGAGGCTCATT-3';     (SEQ ID NO: 31)

O. sativa PBZ1 (D38170) forward primer:
5'-AAGCTCAAGTCACACTCGAC-3';          (SEQ ID NO: 32)

O. sativa PBZ1 (D38170) reverse primer:
5'-GATGTCCTTCTCCTTCTCC-3'.           (SEQ ID NO: 33)
```

For normalization, the actin primers are:

```
O. sativa OsAc1D (X15865) forward primer:
5'-CTTCATAGGAATGGAAGCTGCGGGTA-3';    (SEQ ID NO: 34)

O. sativa OsAc1D (X15865) reverse primer:
5'-GACCACCTTGATCTTCATGCTGCTA-3'.     (SEQ ID NO: 35)
```

FIG. 10A shows the over-expression of OsRHC1 in the transgenic rice lines as measured by real-time PCR. Western blot analysis conducted as described in Example 2, gives the results shown in FIG. 10B. Transformants generally exhibited higher protein content than wildtype.

Figure 11:
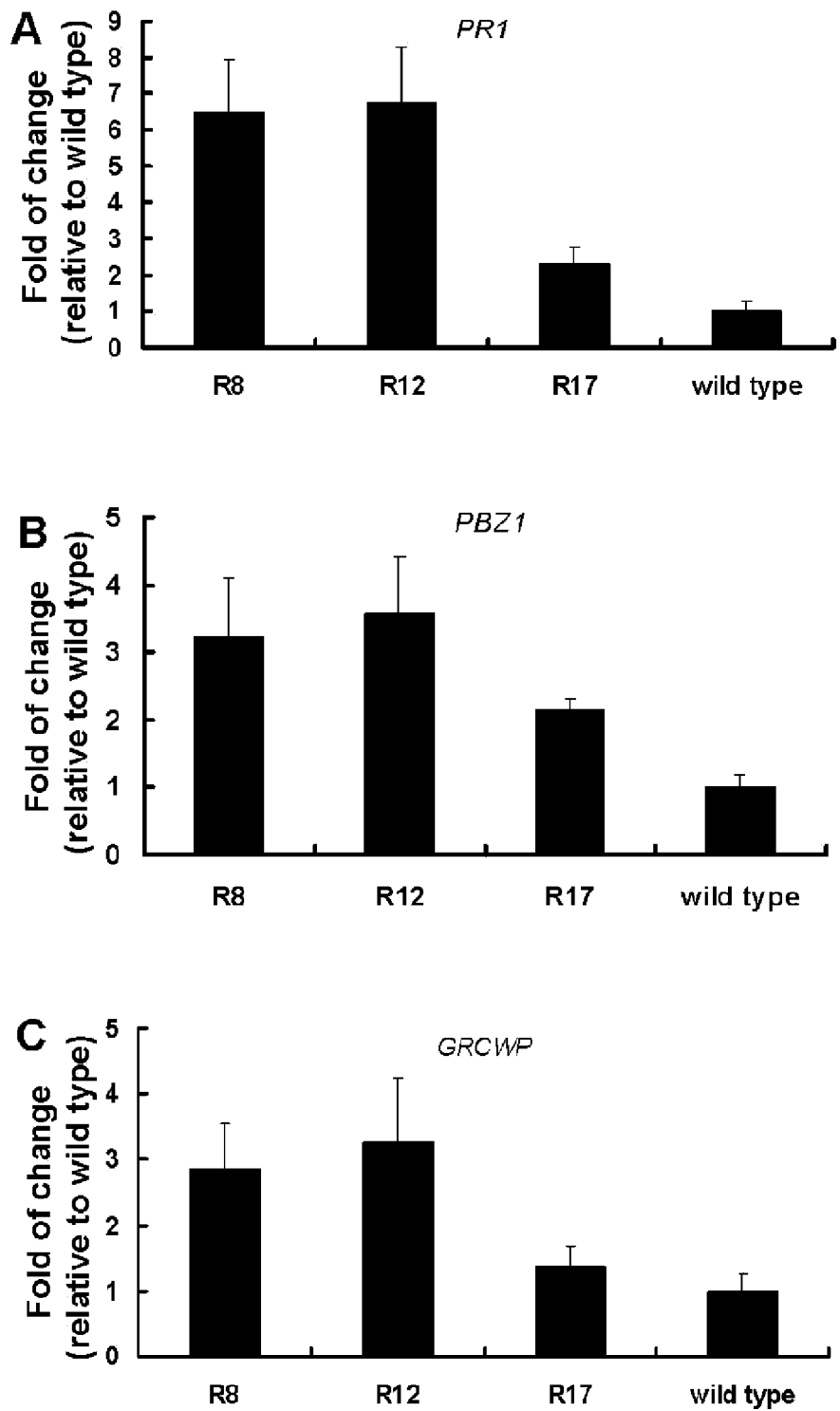
FIGS. 11A-C show expression of defense marker genes PR1 (A), PBZ1 (B) and GRCWP (C) in OsRHC1 transgenic rice lines.

FIG. 11 shows an induction effect by overexpressing OsRHC1 on the expression of the three rice defense marker genes. In general, the degree of induction of the three defense marker genes is positively correlated with the level of OsRHC1 expression. For instance, the two transgenic lines R8 and R12 which exhibited higher level of OsRHC1 also induced the expression of the three defense marker genes to a larger extent (comparing FIGS. 10 and 11).

EXAMPLE 9

OsRHC1 is an E3 Ubiquitin Ligase

This example demonstrates that OsRHC1 is capable of autoubiquitination, a property common to ubiquitin E3 ligases.

A partial fragment of OsRHC1 (OsRHC1p) lacking transmembrane domain located at the N-terminus was prepared. Only the RING-HC domain at the C-terminus is included as the presence of the transmembrane domains makes extraction from *E. coli* cells difficult.

The appropriate C-terminal portion of the encoding sequence was amplified with primer set HMOL5743 (5'-CCGGAATTCGTTGTTCTACTATTACGAAATGG-3') (SEQ ID NO:36) and HMOL2625 (5'-CAGGTCGACGT-TAAACATCATATACGGGCATG-3') (SEQ ID NO:37) flanking the C-terminal half containing the RING-HC domain. The PCR reaction was run with the following cycle profile: 94° C. 5 min; 30 cycles of 94° C. 30 s, 55° C. 30 s and 72° C. 1 min; followed with 72° C. extension for 5 min. The amplified product was subcloned into pGex-4T-1 vector with EcoRI and XhoI restriction sites so as to be fused with GST coding region in frame. The fusion protein was then expressed in DE3 cell with 1.5 mM IPTG induction at 30° C. for 2 hours during growth phase. GST-OsRHC1p protein was extracted by lysing the bacterial cells with 1 mg/ml lysozyme at room temperature for 1 hour, followed by 5 freeze/thaw cycles with liquid nitrogen and warm water bath. The extracted protein was purified with GST SpinTrap™ Purification Module (GH Healthcare).

The in vitro ubiquitination assay was performed in ubiquitination buffer (40 mM Tris-HCl (pH 7.5), 5 mM MgCl, 2 mM ATP, 2 mM dithiothreitol, 300 ng/μl ubiquitin, 25 μM MG132, 5 μl wheat germ extract (to provide E1 and E2 enzymes) (Promega)) plus either 400 ng GST-OsRHC1p or GST only protein. As negative control, the same reaction buffer without the addition of ATP and ubiquitin was used (modified as described by Bazirgan, O. A., et al., *J. Biol. Chem.* (2006) 281:38989-39001; Matsuda, N., et al., *J. Cell. Sci.* (2001) 114:1949-1957). The reaction mixtures were kept at room temperature for 2 hours, then subjected to 10% SDS-PAGE gel electrophoresis, and followed by Western blot analysis with anti-OsRHC1 specific antibody. (FIG. 12).

Autoubiquitination of GST-OsRHC1 was observed in the reaction including ATP and ubiquitin (+ve), but not in the reaction without ATP and ubiquitin (-ve).

These results demonstrate that, like other E3 ligases, OsRHC1 undergoes autoubiquitination.

EXAMPLE 10

Identification of an OsRHC1 Binding Partner

A protein encoded by a clone deposited in GenBank Accession No. ABA98865.1 was identified as a binding partner. This was ascertained using a yeast two hybrid protocol and verified by co-precipitation. The protein encoded by this deposited clone is expressed in *Oryza sativa* (Japonica Cultivar-Group) but it has no identified function. However, since it interacts with OsRHC1, it is presumed to modulate plant defense responses.

The yeast two hybrid protocol employed a commercial kit, the BD Matchmaker™ library construction and screening kit (Clontech K1516-1). OsRHC1 was first amplified with the oligos HMOL2624 (5'-CCGAATTCATGCCAGCCCCT-TCGCTTC-3') (SEQ ID NO:38) and HMOL2625 (5'-CAG-GTCGACGTTAAACATCATATACGGGCATG-3') (SEQ ID NO:39), digested with the EcoRI and SalI, subcloned into pGBKT7 in reading frame and transformed into yeast strain Y187. Proteins were extracted from the yeast clones transformed with pGBKT7-OsRHC1 and the control pGBKT7. Western blot analysis with anti-c-Myc epitope tag antibody confirms the presence of DNA binding domain fused OsRHC1 proteins.

Samples of RNA from several rice lines (each containing one of the following R genes: Xa2, Xa12, Xa14, Pita, Pib, and Pik) inoculated with the corresponding incompatible pathogens (T2 for Xa2; P1 for Xa12; LN44 for Xa14; Ken54-04 for Pita, Pib and Pik) for 4 days were used as starting materials to construct an AD domain fusion yeast library in the yeast strain AH109 according to the manufacturer's manual. Two rounds of library screening were performed by mating between pGBKT7-OsRHC1 transformed Y187 and the AH109 yeast library. Yeast diploid mating products were selected on SD minus Trp, Leu and His (SD/-3) agar plates and incubated at 30° C. for 4 days. Only colonies grown to 2-3 mm diameter were further streaked onto SD minus Trp, Leu, His and Ade (SD/-4) agar plates. Selected clones were tested by colony-lift filter assay for lacZ reporter gene activity (*Yeast Protocols Handbook*, Clontech PT3024-1). The partial clone that encoded expressed protein (accession number: ABA98865.1) (labeled as HML1797) produced a positive result. Retransformation of pGBKT7-OsRHC1 and pGADT7-HML1797 into AH109 confirmed this was not due to mutation.

To verify the result of yeast-2-hybrid experiments, co-immunoprecipitation assays were conducted. The full-length coding region of ABA98865.1 was amplified with primers HMOL5311 (5'-AACCCGGGATGGCCGTGGGGTCA-GAG-3') (SEQ ID NO:40) and HMOL5312 (5'-TTC-CCGGGTCAAAATAAAAACAAATAAAAAAACAC-3') (SEQ ID NO:41), digested with SmaI and subcloned into SmaI linearized pGADT7-Rec vector to generate a fusion protein with an in-frame HA tag (HA-ABA98865.1); this was designated HML1846. This construct was transcribed and translated in vitro by RiboMAX RiboMAX™ large scale RNA production systems-T7 (Promega), wheat germ extract (Promega) and Transcend™ biotin-lysyl-tRNA system (Promega) in combination, respectively.

Total protein was extracted from a rice line overexpressing OsRHC1 (modified from Boyes, D. C., et al., *Proc. Natl. Acad. Sci. USA* (1998) 95:15849-15854; Greve, K., et al., *Biochem. J.* (2003) 371:97-108. Samples from rice containing 100 μg protein were mixed with 40 μl HA tag fused protein above in a co-immunoprecipitation buffer containing 50 mM Tris/HCl (pH 7.5), 250 mM NaCl, 2 mM $MgCl_2$, 0.5 mM $CaCl_2$, 10% (v/v) glycerol, 1.5% (v/v) Triton® X-100, 1 mM PMSF, 2 mg/L leupeptin (modified from Boyes, et al., 1998, supra; Greve, et al., 2003, supra), using the BD Matchmaker™ Co-IP Kit (Clontech 630449). Anti-HA epitope tagged antibody was employed for pulling down the protein complexes. Protein signal was detected by anti-OsRHC1 antibody.

Western blot showed that OsRHC1 was pulled down by HA tag fused ABA98865.1, but no protein was detected on Western blot when the rice protein extract was treated with unrelated protein fused with HA tag.

The invention claimed is:

1. A recombinant expression system that comprises a nucleotide sequence encoding a protein that has the amino acid sequence of SEQ ID NO:43.

2. A plant or plant cell modified to contain the expression system of claim 1.

3. A method to confer an enhanced ability to resist infections or wounding on a plant, which method comprises modifying said plant to contain the expression system of claim 1.

4. A method to prepare a protein that has the amino acid sequence of SEQ ID NO:43, which method comprises culturing cells that comprise the expression system of claim 1 under conditions wherein said protein is produced and recovering the protein from the culture.

5. A method to confer an enhanced ability to resist infections or wounding on a plant, which method comprises modifying said plant to contain a recombinant expression system that comprises a nucleotide sequence encoding a protein that has the amino acid sequence of SEQ ID NO:43 or a variant thereof that is at least 95% identical to said amino acid sequence and that confers on plants resistance to infection or wounding, wherein the nucleotide sequence is operatively linked to control systems that effect expression in plant cells, and
wherein said plant is identified as in need of said enhanced ability.

6. The method of claim 5 wherein said variant is at least 98% identical to said amino acid sequence.

7. The method of claim 6 wherein said variant is at least 99% identical to said amino acid sequence.

* * * * *